United States Patent
Chen et al.

(10) Patent No.: US 10,780,070 B2
(45) Date of Patent: Sep. 22, 2020

(54) ALPHA-AMINOADIPATE FOR TREATMENT OF VISION LOSS AND RESTORING SIGHT

(71) Applicant: The Schepens Eye Research Institute, Inc., Boston, MA (US)

(72) Inventors: Dong Feng Chen, Newtonville, MA (US); Kin-Sang Cho, Winchester, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 385 days.

(21) Appl. No.: 15/029,507

(22) PCT Filed: Oct. 20, 2014

(86) PCT No.: PCT/US2014/061381
§ 371 (c)(1),
(2) Date: Apr. 14, 2016

(87) PCT Pub. No.: WO2015/058197
PCT Pub. Date: Apr. 23, 2015

(65) Prior Publication Data
US 2016/0271091 A1  Sep. 22, 2016

Related U.S. Application Data

(60) Provisional application No. 61/892,822, filed on Oct. 18, 2013.

(51) Int. Cl.
*A61K 31/198* (2006.01)
*A61K 9/00* (2006.01)
*A61K 35/30* (2015.01)
*A61K 31/42* (2006.01)

(52) U.S. Cl.
CPC .......... *A61K 31/198* (2013.01); *A61K 9/0019* (2013.01); *A61K 9/0048* (2013.01); *A61K 31/42* (2013.01); *A61K 35/30* (2013.01)

(58) Field of Classification Search
CPC .............................. A61K 31/19; A61K 31/198
See application file for complete search history.

(56) References Cited

U.S. PATENT DOCUMENTS

| 3,773,919 | A | 11/1973 | Boswell et al. | |
|---|---|---|---|---|
| 2005/0152995 | A1* | 7/2005 | Chen | A61K 31/00 424/722 |
| 2006/0177430 | A1 | 8/2006 | Bhushan et al. | |
| 2009/0298785 | A1 | 12/2009 | Dyer et al. | |

FOREIGN PATENT DOCUMENTS

WO    2015/058197 A1    4/2015

OTHER PUBLICATIONS

Lorber et al., Activated retinal glia mediated axon regeneration in experimental glaucoma, 2012, Neurobiology of Disease, vol. 45, pp. 243-252. (Year: 2012).*
Brown, The Glio-toxic mechanism of alpha-aminoadipic acid on cultured astrocytes, 1998, Journal of Neurocytology, vol. 27, pp. 109-118. (Year: 1998).*
Takeda et al, alpha-aminoadipate induces progenitor cell properties of Muller glia in adult mice, 2008, Invest Ophthalmol Vis Sci, vol. 49, No. 3, pp. 1142-1150. (Year: 2008).*
Shen et al. Retinal Vascular changes after Glial disruption, 2010, Journal of Neuroscience Research, vol. 88, pp. 1485-1499. (Year: 2010).*
Takeda et al., Investigative Ophthalmology & Visual Science, 2008, 49(3): 1142-50.*
Bertelsen et al. (May 9, 2013) "Prevalence and Diagnostic Spectrum of Generalized Retinal Dystrophy in Danish Children", Ophthalmic Epidemiology, 20(3):164-169.
Bringmann et al. (Nov. 2009) "Cellular Signaling and Factors Involved in Müller Cell Gliosis: Neuroprotective and Detrimental Effects", Progress in Retinal and Eye Research, 28(6):423-451.
Grimm et al. (May 2000) "Protection of Rpe65-Deficient Mice Identifies Rhodopsin as a Mediator of Light-Induced Retinal Degeneration", Nature Genetics, 25:63-66.
Kinouchi et al. (Aug. 2003) "Robust Neural Integration from Retinal Transplants in Mice Deficient in GFAP and Vimentin", Nature Neuroscience, 6(8):863-868.
Kriss et al. (Jul. 1992) "The Electroretinogram in Infants and Young Children", Journal of Clinical Neurophysiology, 9(3):373-393.
Nih "Retinitis Pigmentosa", National Eye Institute, Last Updated on Jul. 10, 2019, retrieved on Feb. 10, 2020, 8 pages.
Reme et al. (Jan. 2003) "Why Study Rod Cell Death in Retinal Degenerations and How?", Documenta Ophthalmologica, 106(1):25-29.
Takeda et al. (May 2005) "Glutamate Stimulates Neurogenesis and Photoreceptor Cell Regeneration in the Adult Mouse Retina", Investigative Ophthalmology & Visual Science, 46(13):1 page.
Tang et al. (2015) "Haplotypes of RHO Polymorphisms and Susceptibility to Age-Related Macular Degeneration", International Journal of Clinical and Experimental Pathology, 8(3):3174-3179.
Wikipedia "Electroretinography", https://en.wikipedia.org/wiki/Electroretinography, retrieved on Mar. 11, 2020, 4 pages.

* cited by examiner

Primary Examiner — Rei Tsang Shiao
(74) Attorney, Agent, or Firm — Mintz Levin Cohn Ferris Glovsky and Popeo, P.C.; Ingrid A. Beattie; Nicholas A. Zachariades

(57) ABSTRACT

The invention provides compositions and methods for preserving, restoring, or enhancing vision of a subject by administering compositions to an injured or diseased eye.

14 Claims, 29 Drawing Sheets

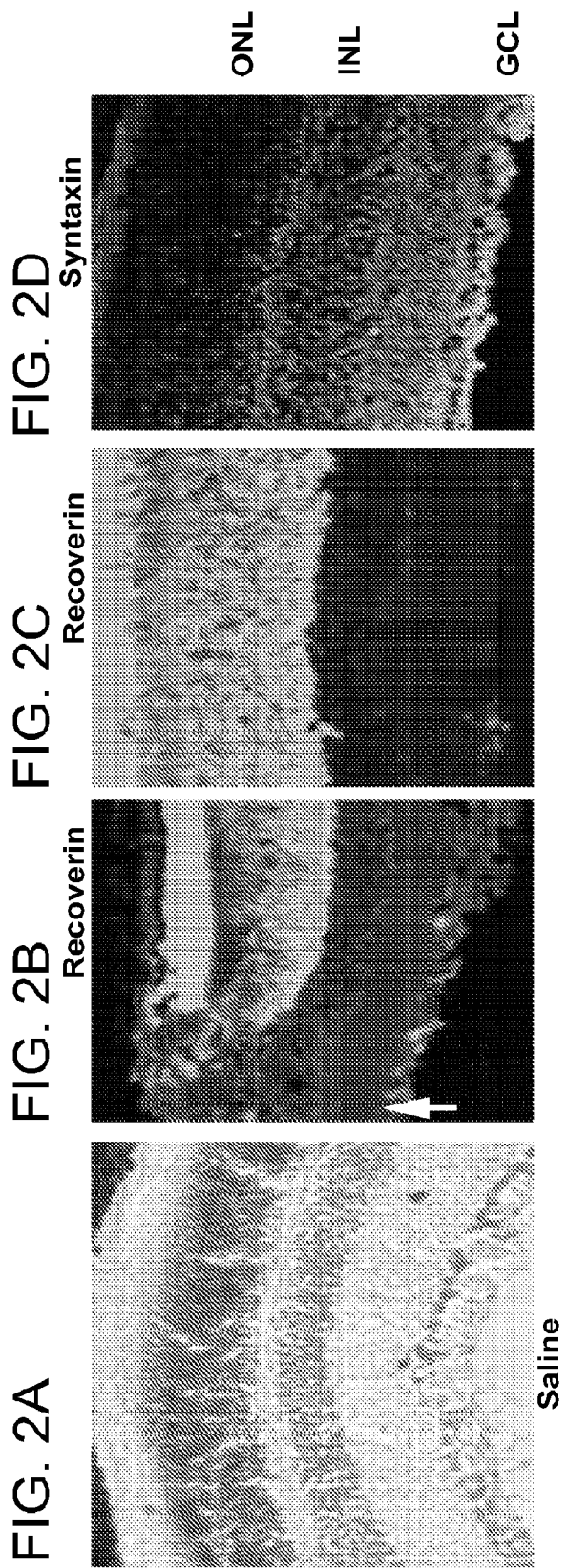

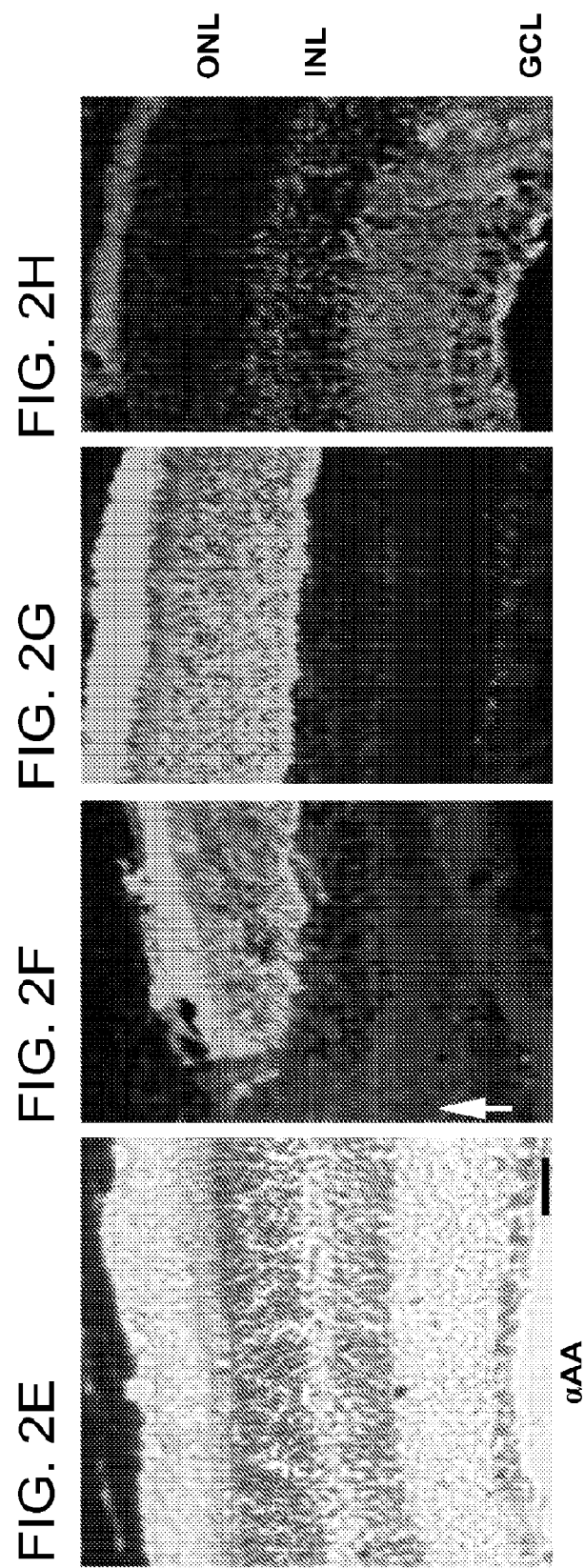

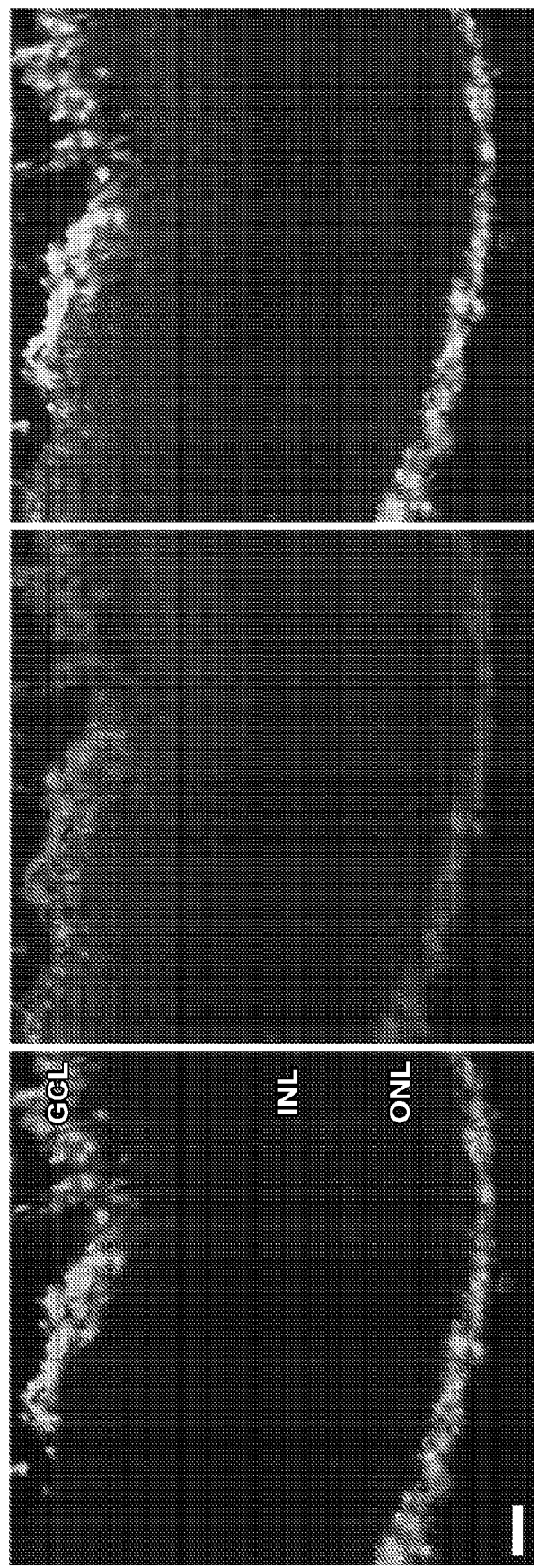

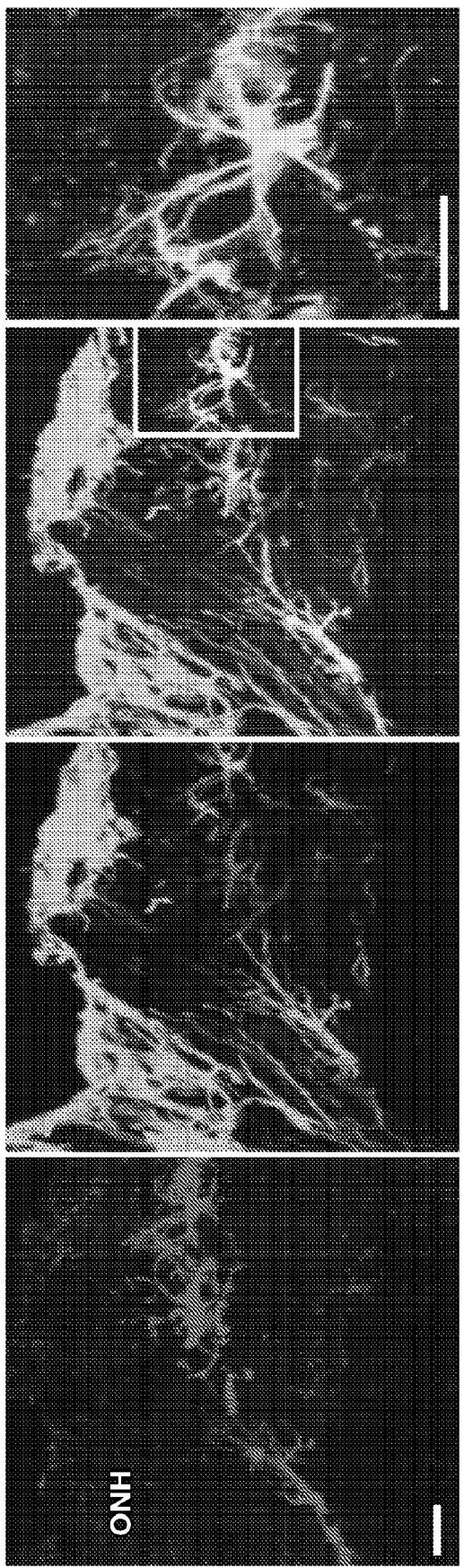

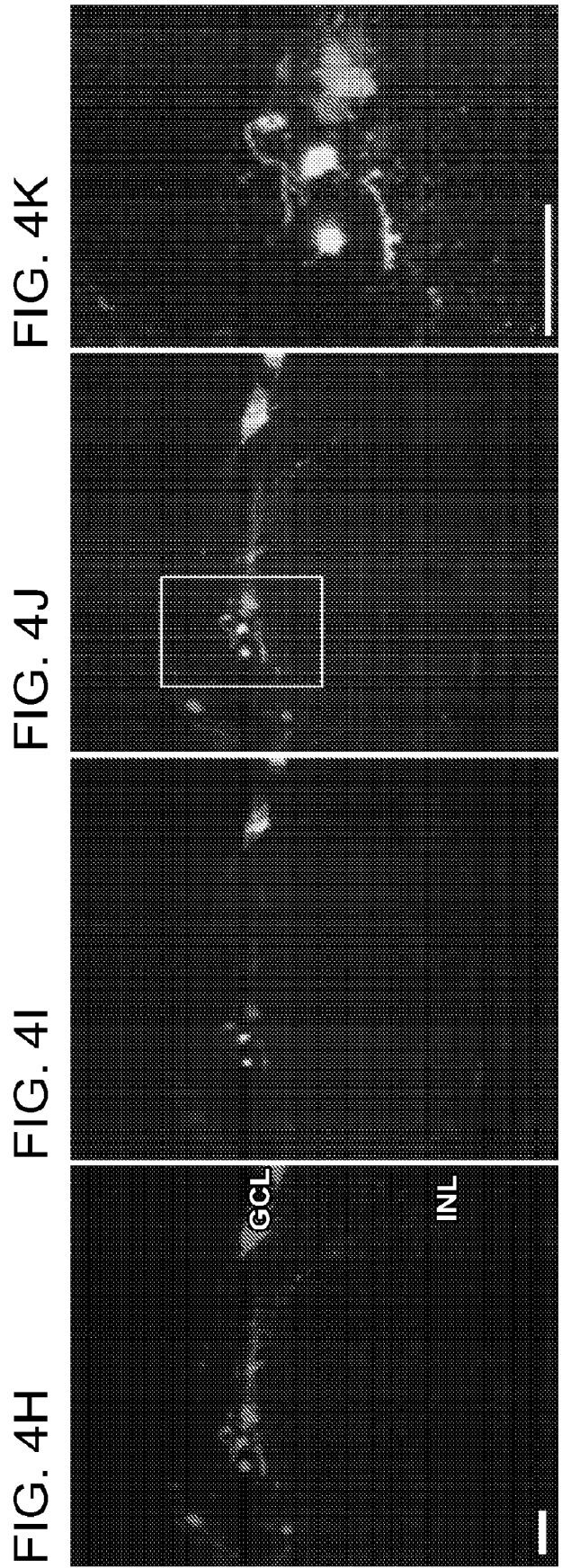

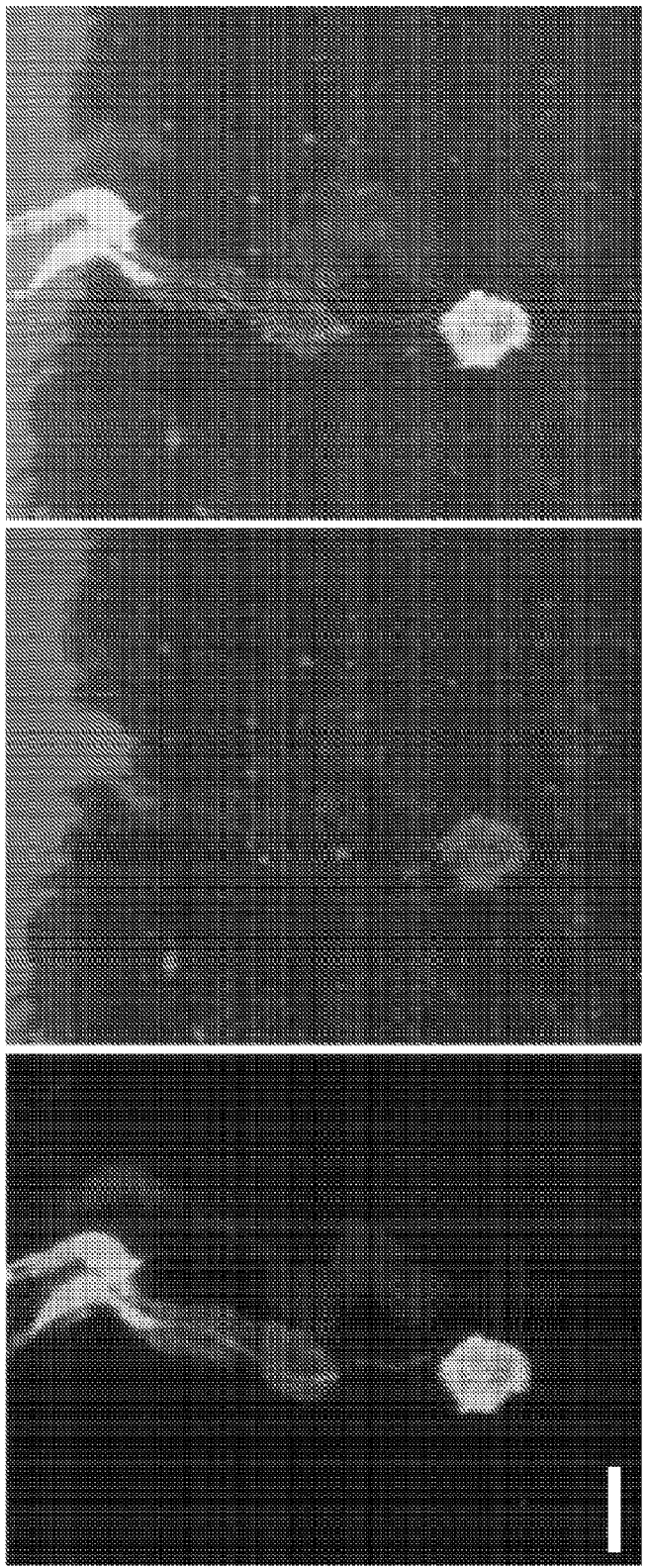

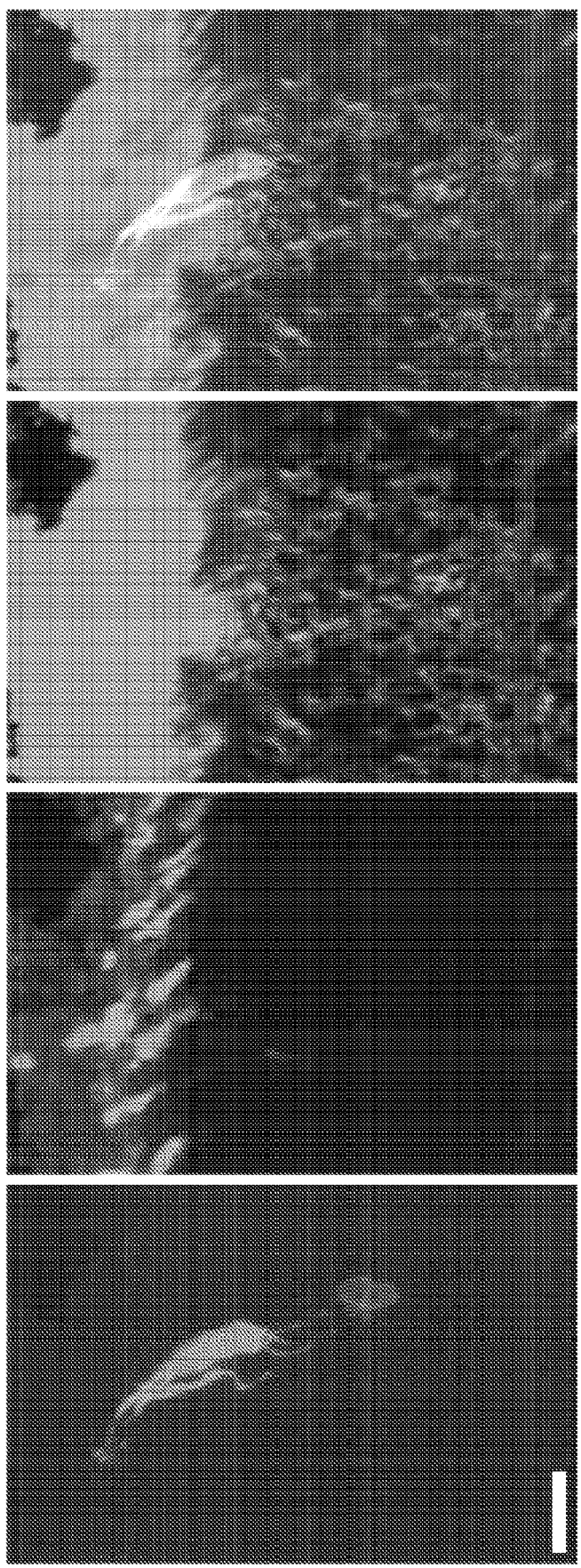

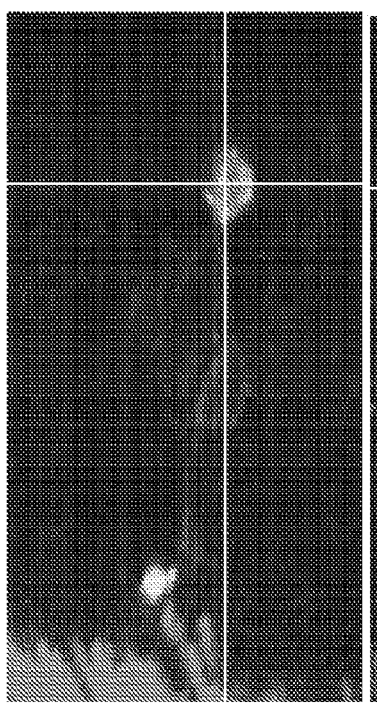
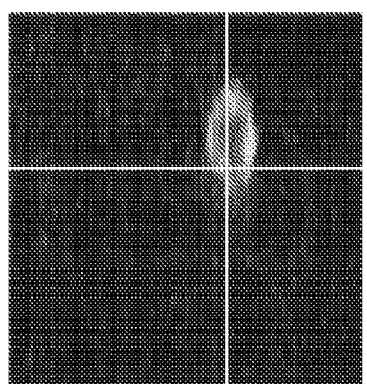
FIG. 6A
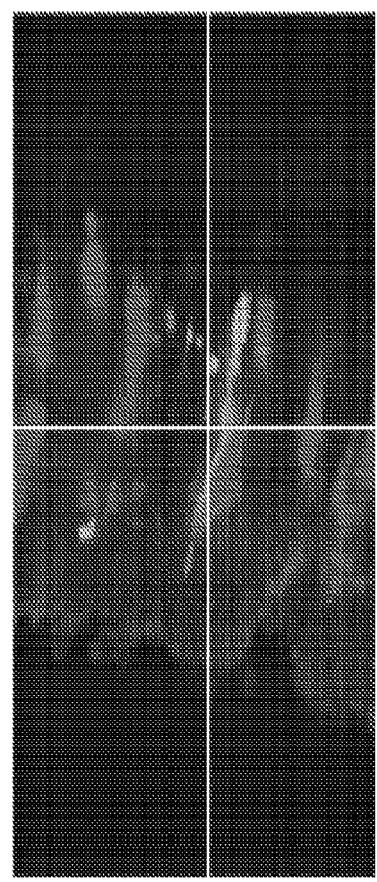
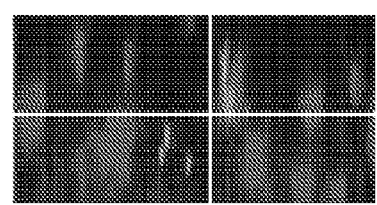
FIG. 6B

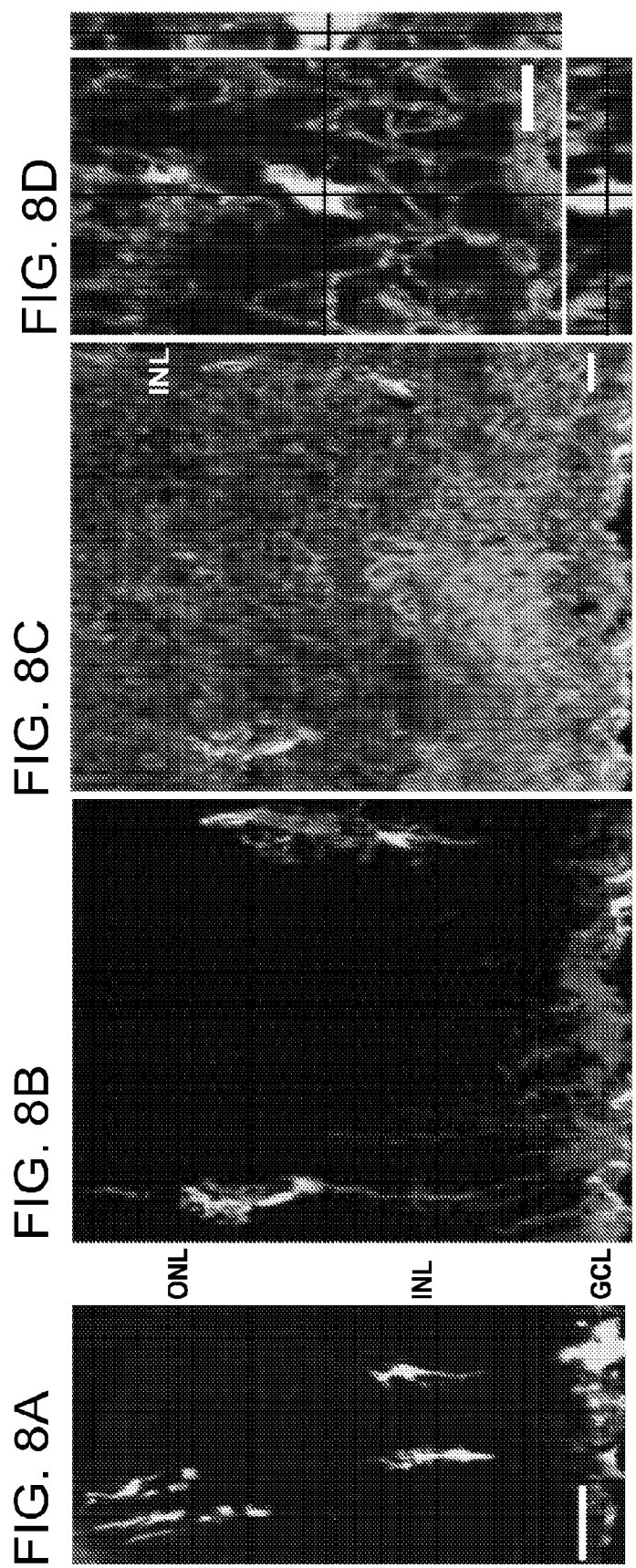

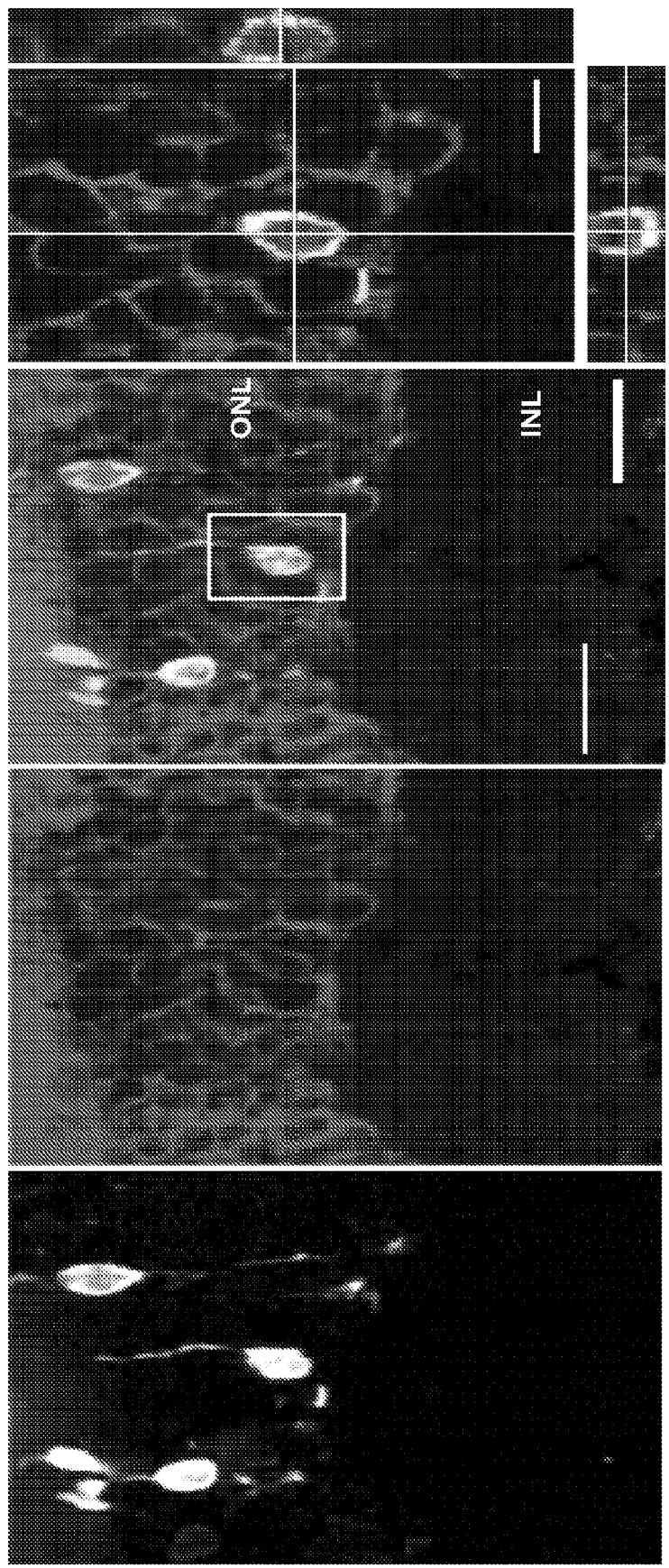

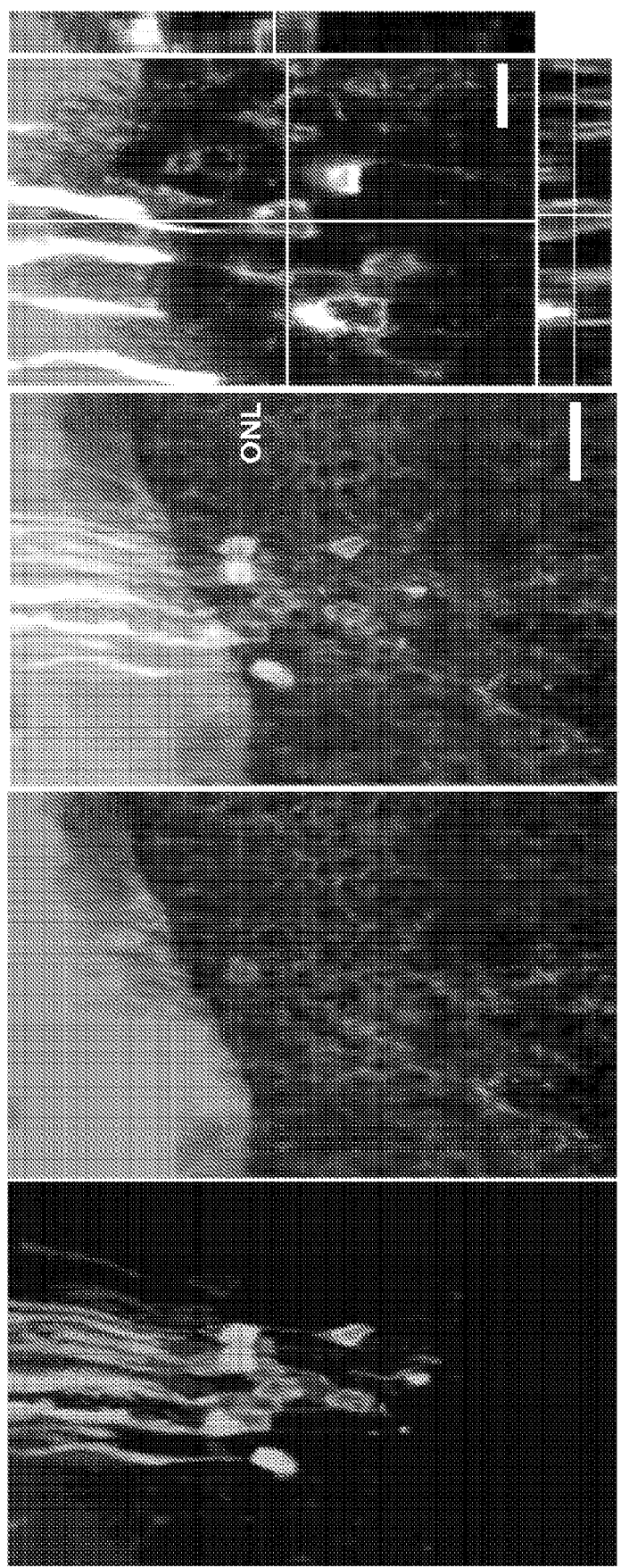

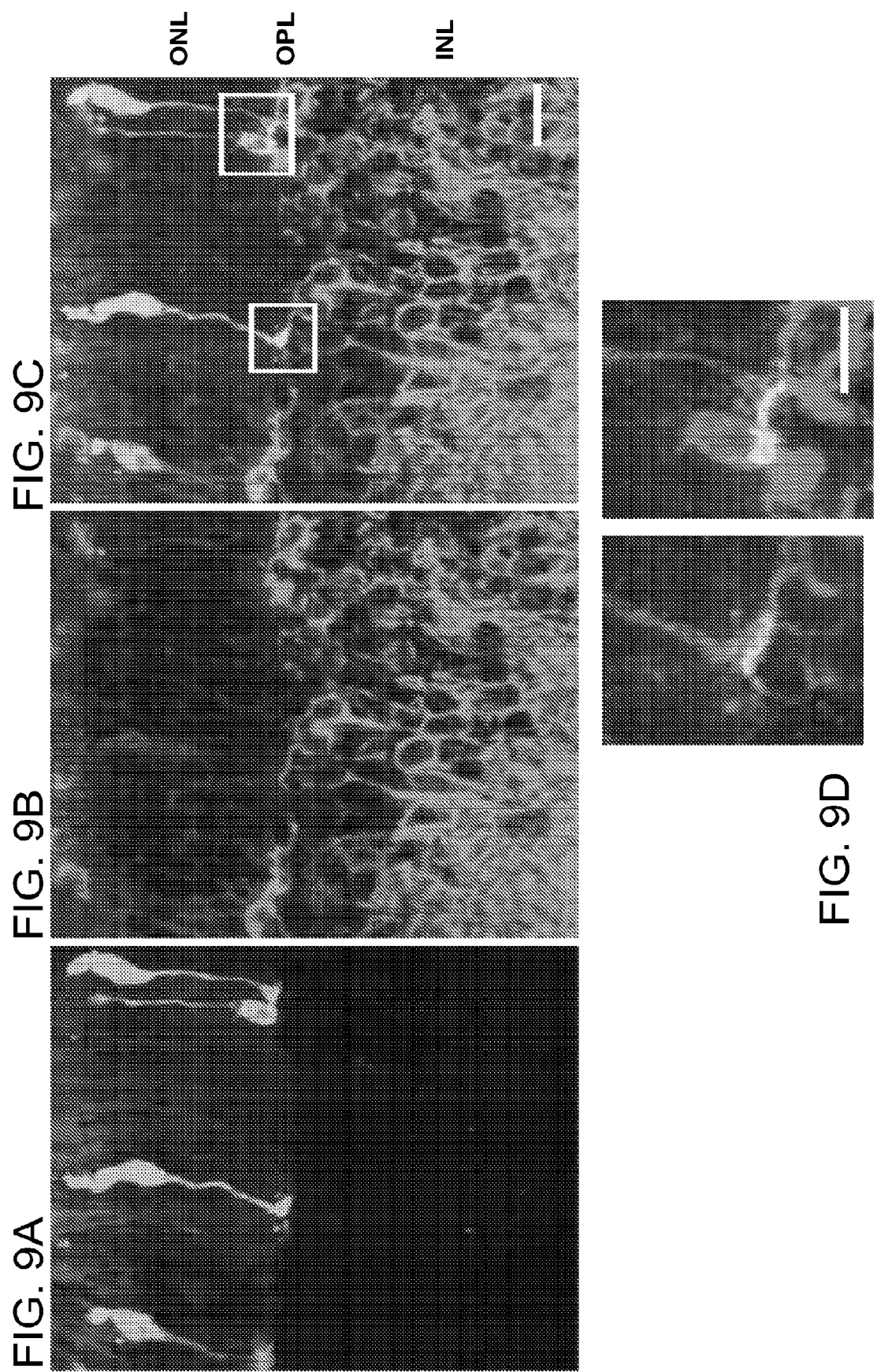

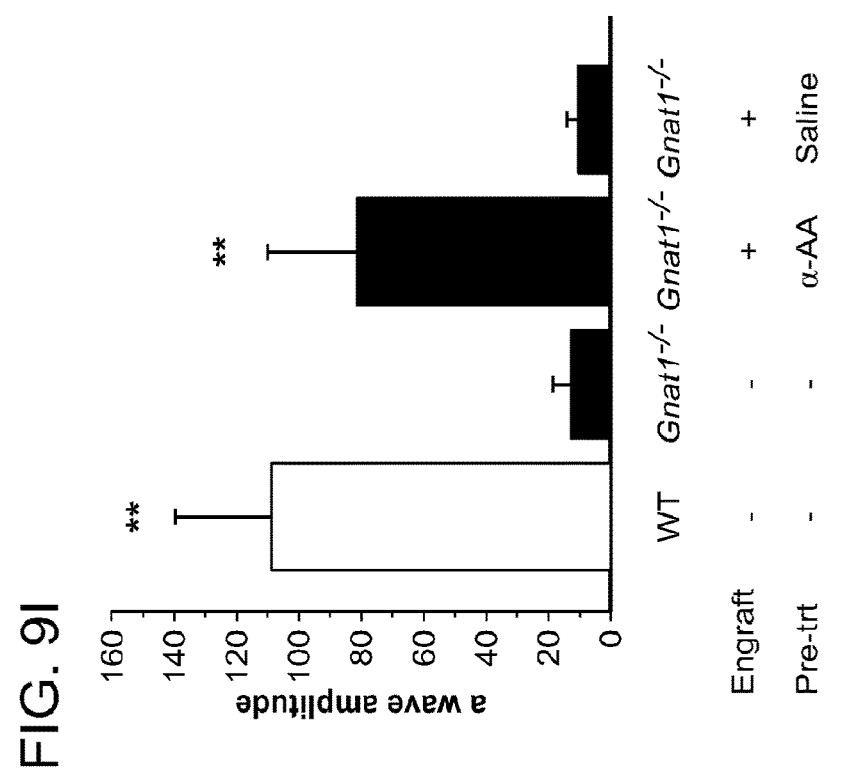
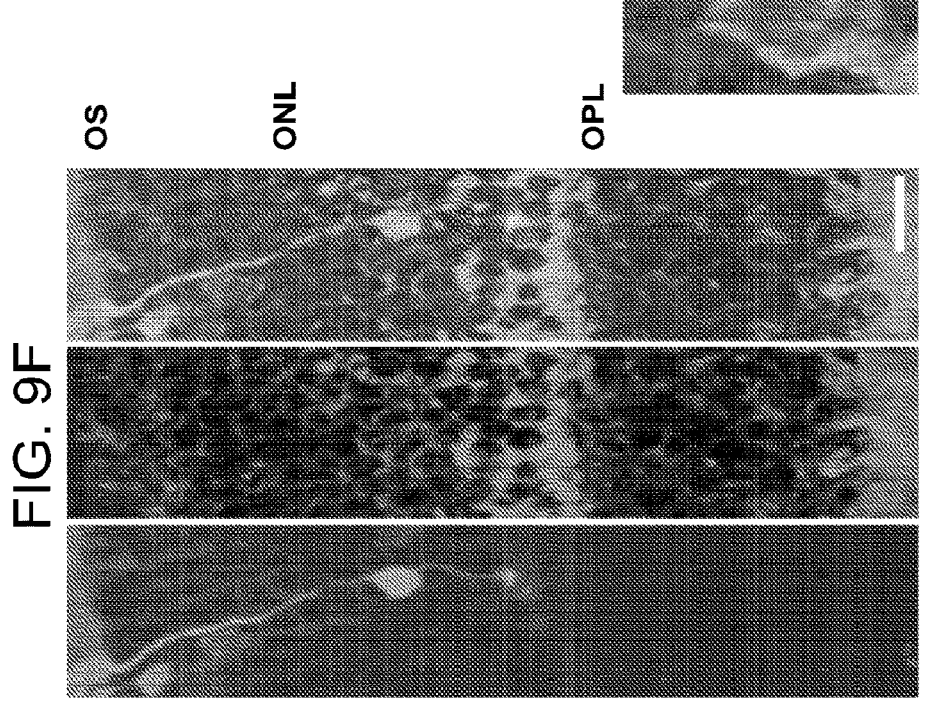

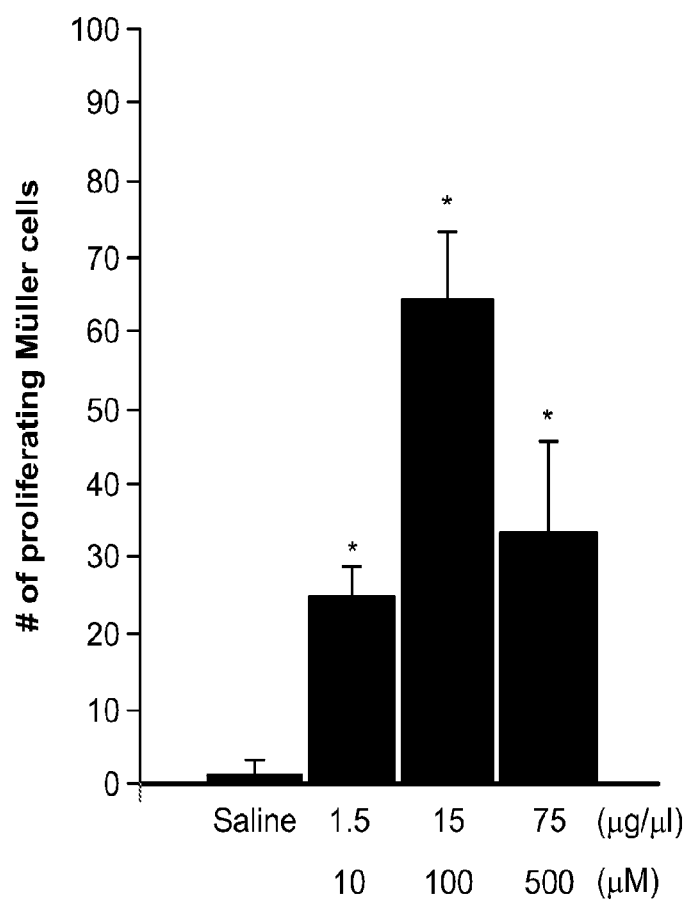

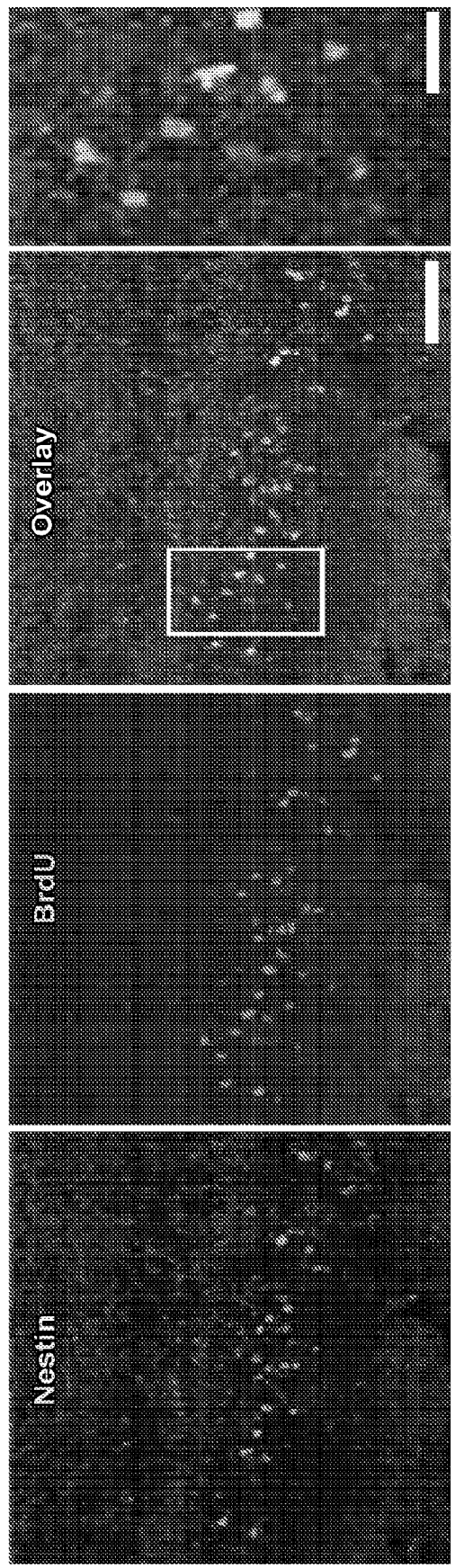

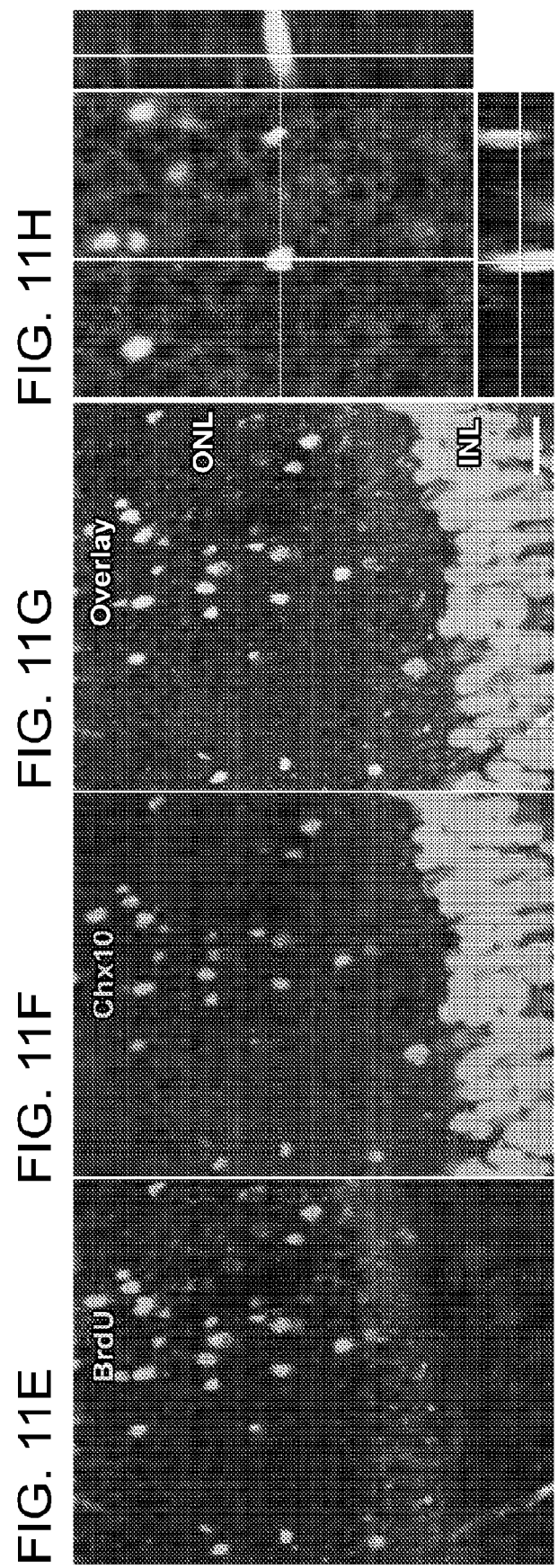

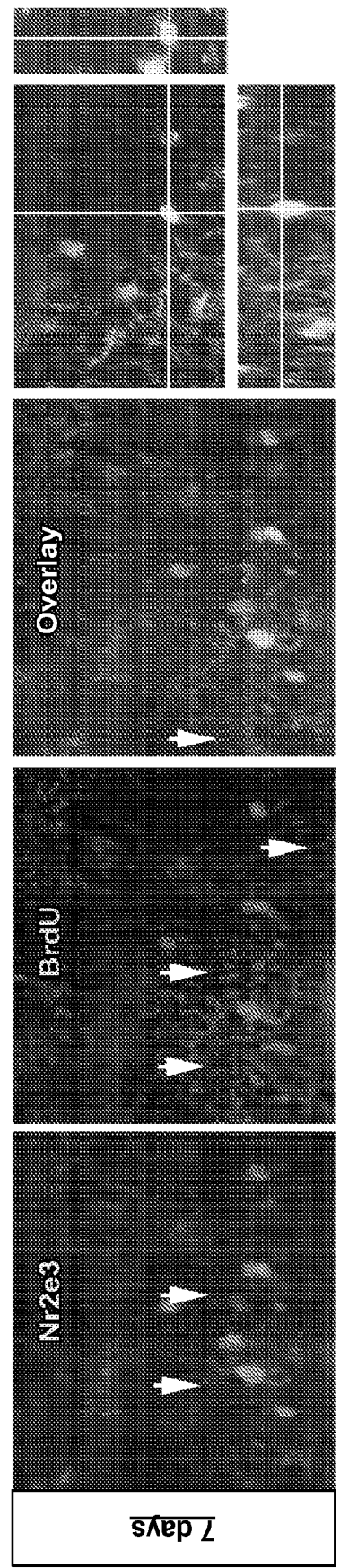

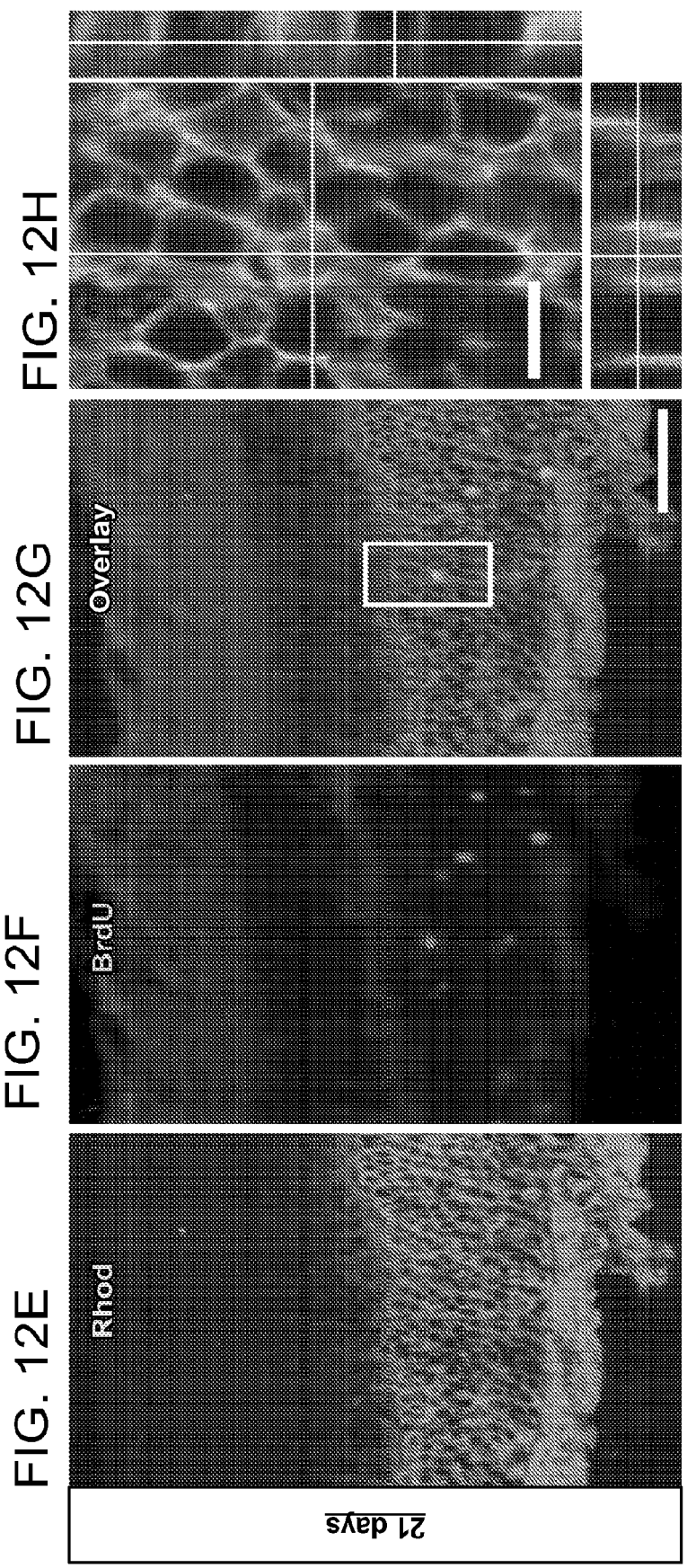

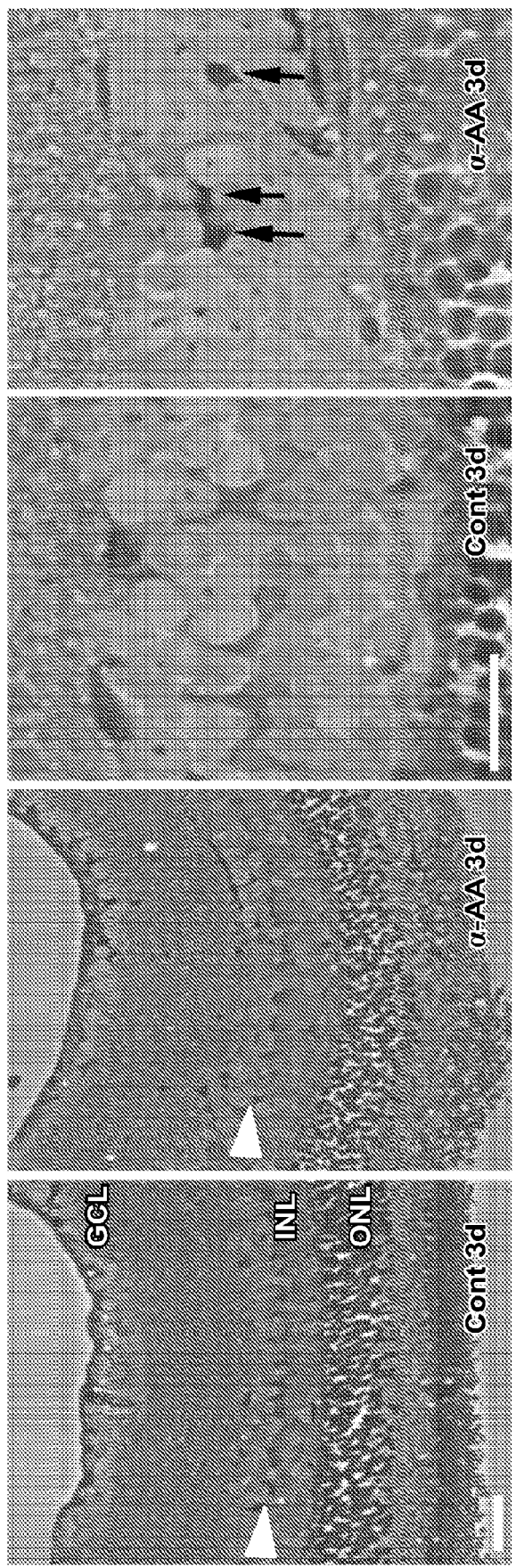
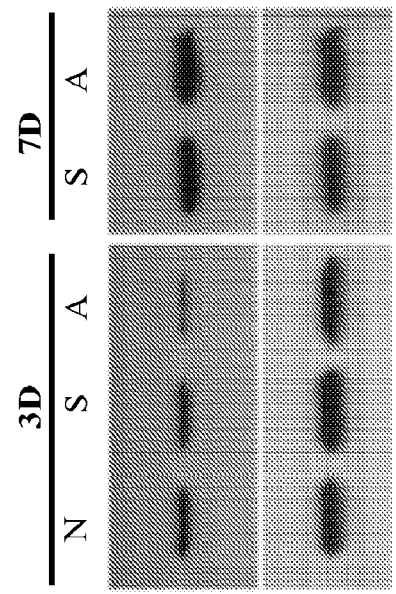
FIG. 13A FIG. 13B FIG. 13C FIG. 13D
FIG. 13E

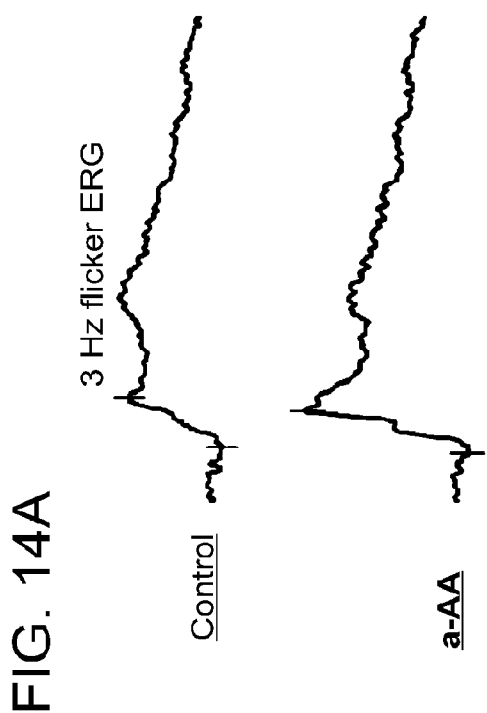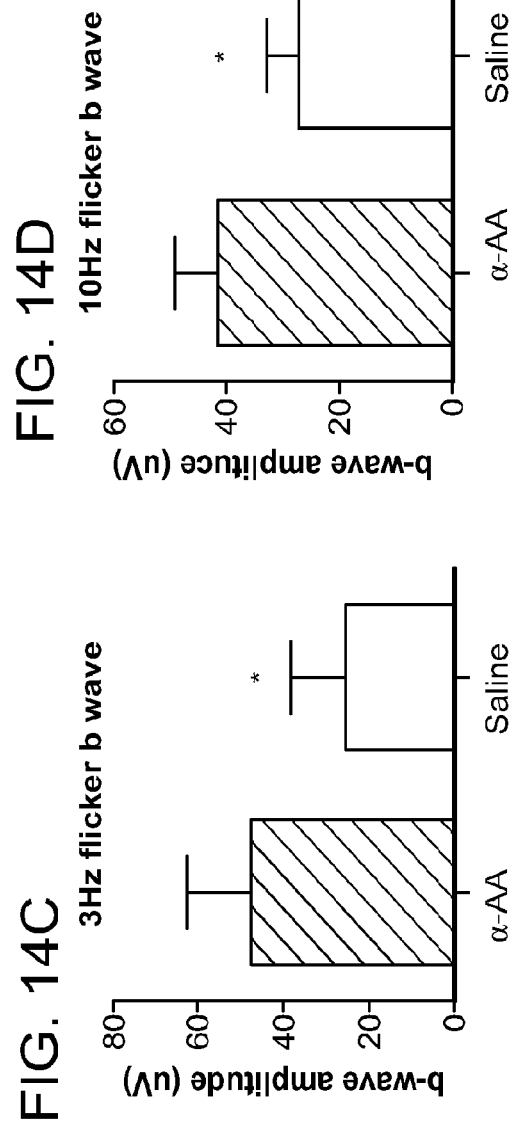

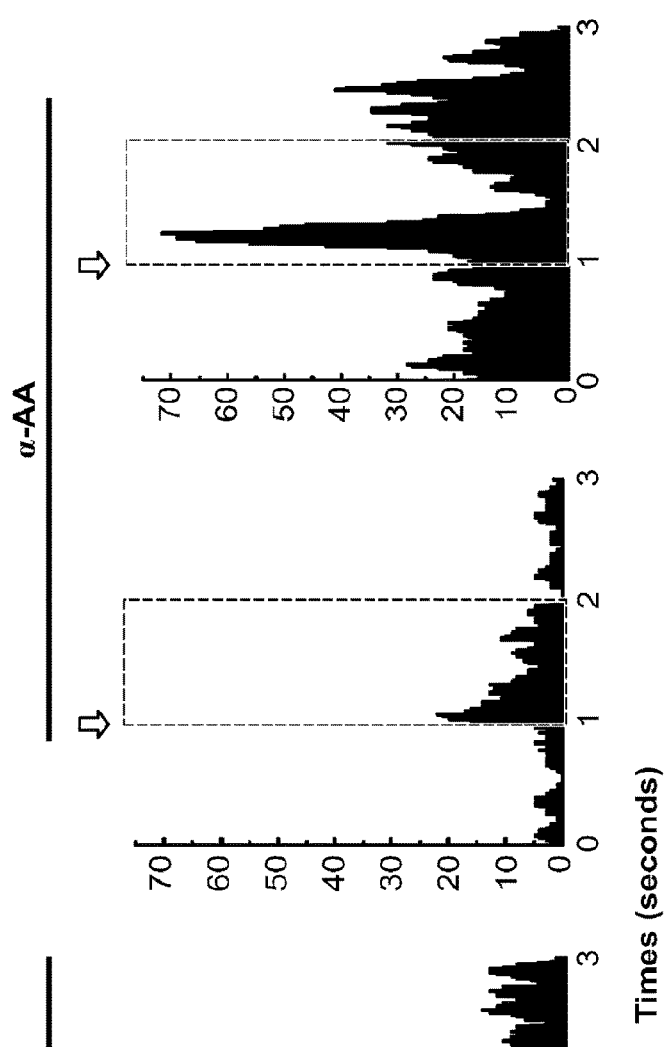
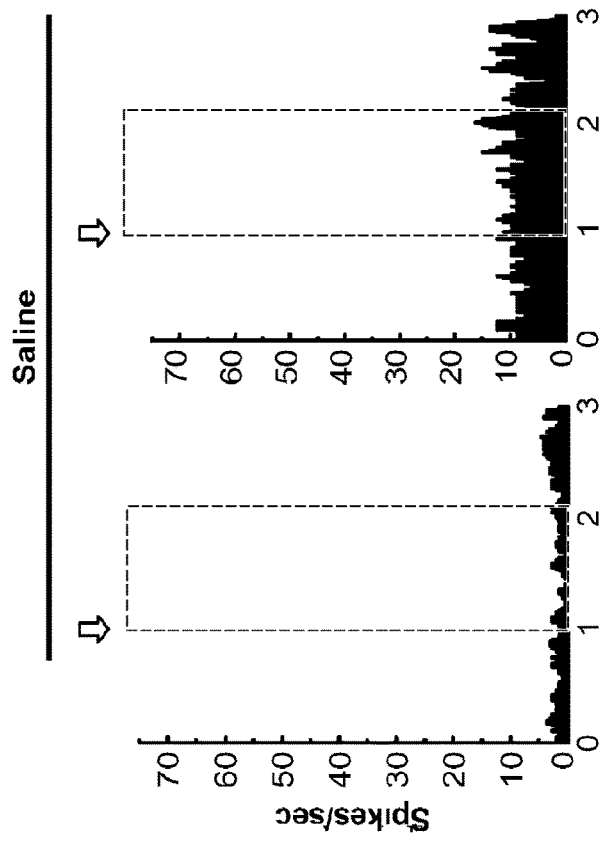
FIG. 15A
FIG. 15B

ALPHA-AMINOADIPATE FOR TREATMENT OF VISION LOSS AND RESTORING SIGHT

CROSS-REFERENCE TO RELATED APPLICATIONS

The present application is a national stage application, filed under U.S.C. § 371, of International Application No. PCT/US2014/061381, filed on Oct. 20, 2014, which claims benefit of priority to U.S. Provisional Application No. 61/892,822 filed Oct. 18, 2013 and incorporates the disclosure of each of the applications herein by reference in its entirety.

FIELD OF THE INVENTION

This invention relates generally to the field of ophthalmology.

BACKGROUND OF THE INVENTION

The burden of mortality and morbidity that vision loss and blindness impose on society makes it a pressing public health and medical problem. Current therapeutic strategies for treating loss of vision caused by retinal cell damage almost all have been directed to controlling the cause of the illness or neuron death rather than reversing retinal neuron damage or replacing lost cells. For example, anti-VEGF therapy for age-related macular degeneration (AMD) targets abnormal ocular vascularization and eye drops that lower intraocular pressure for treating glaucoma, but such therapies fail to address the lost or degenerated cells. To date, there are no treatments that stimulate the retina to regenerate new cells endogenously. Retinal cell transplantation as a therapeutic strategy to replace lost cells is emerging as a promising approach, however challenges and technical hurdles still remain. Thus, there is an urgent need for new treatment options for reversing retinal neuron damage and/or replacing lost cells for preserving, restoring, or enhancing vision.

SUMMARY OF THE INVENTION

The present disclosure is based on the surprising discovery that alpha-aminoadipate (α-AA) stimulates proliferation and trans-differentiation of retinal cells to retinal progenitor cells, creates a retinal environment permissive for photoreceptor differentiation by progenitor cells, ultimately resulting in the increased or restored photoreceptor activity/function and restoration of vision.

Accordingly, compositions for preserving, restoring, or enhancing vision of a subject comprising alpha-aminoadipate or a functional analog thereof are described herein. Methods for preserving, restoring, or enhancing vision of a subject, comprising administering to an injured or diseased eye of said subject a composition comprising alpha-aminoadipate or a functional analog thereof are also described herein. The less invasive chemical- or drug-based strategy of mobilizing endogenous stem cells to repair neural damage presents many advantages over the transplantation approach including decreased risk of immune rejection, neuron integration, and tumor formation.

As α-AA treatment creates an environment permissive for cell integration and photoreceptor generation, also disclosed herein are compositions for enhancing the efficacy of cell replacement or transplantation in an injured or diseased eye of a subject to the eye of the subject prior to transplantation of exogenous cells. The replacement or transplanted cells are retinal cells, for example, retinal stem cells, retinal progenitor cells, or retinal stem cell-derived neural cells. The cells may be autologous or genetically engineered. As used herein, "enhancing efficacy" relates to increasing engraftment or integration of exogenous retinal cells, increasing photoreceptor activity, or increasing photoreceptor cells. For example, enhancement comprises at least 10%, 20%, 50% or 2-fold, 5-fold, 10-fold, or more of the number or activity of engrafted cells compared to the level in the absence of alpha-aminoadipate. The composition increases the mobility and migration of the endogenous retinal cells. The composition is administered prior to, concurrently with, or after cell replacement or transplantation. Methods for enhancing efficacy of retinal cell replacement in an injured or diseased eye of a subject, comprising administering a composition comprising alpha-aminoadipate or functional analog thereof to the eye of the subject prior to transplantation of exogenous retinal cells are also provided herein.

Functional analogs of alpha-aminoadipate include, but are not limited to: glutamate, glutamate agonists, aspartate, homocysteate, N-methylD-aspartate (NMDA), L-ibotenate, and D-ibotenate, α-aminoadipic acid, (2S,4S)-4-methyl-aminoadipate, (2S,5S)-5-methyl-aminoadipate, and (2S,5R)-5-methyl-aminoadipate.

The term "functional analog" includes compounds with the same or comparable physiological activity as a reference agent such as alpha amino-adipate.

As used herein, preserving, restoring, or enhancing vision of a subject relates to increasing photoreceptor activity, increasing photoreceptor regeneration, increasing the number of retinal progenitor cells, increasing the number of retinal neurons, replacing lost or damaged retinal neurons or retinal cells, increasing light retinal response, increasing light perception/detection, increasing visual acuity, or increasing visual contrast. For example, increased number of retinal cells or photoreceptor activity comprises at least 10%, 20%, 50% or 2-fold, 5-fold, 10-fold, or more of the number or activity of engrafted cells compared to the level in the absence of alpha-aminoadipate. For example, the composition increases proliferation, migration, de-differentiation, or trans-differentiation of Muller cells, ciliary epithelial cells, retinal pigment epithelial cells, bone marrow-derived stem cells, mesenchymal stem cells, or iPS cells and iPS-derived retinal progenitor cells. As used herein, "de-differentiation" relates to the process in which a cell of a specific cell type (e.g., a Muller cell) loses at least one cell type-specific (e.g., Muller cell marker), As used herein, "trans-differentiation" relates to the process in which a cell of a specific cell type (e.g., a Muller cell) gains at least one marker of a different cell type (e.g., a marker of a retinal progenitor cell or a photoreceptor cell). Examples of markers for Müller cells include GFAP, CRALBP, and vimentin. Examples of markers for retinal progenitor cells include Nestin and Chx10. Examples of markers for retinal photoreceptor cells include recoverin and rhodopsin.

Methods for measuring or assessing increased photoreceptor activity, increased photoreceptor regeneration, increased number of retinal progenitor cells, increased the number of retinal neurons, replacement of lost or damaged retinal neurons or retinal cells, increased light retinal response, increased light perception/detection, or increased visual acuity are known in the art. For example, electroretinopathy, patch-clamp recording, spectral domain optical coherence tomography (SD-OCT), or visual evoked potential can be used. Electroretinography (ERG) analysis is a method known in the art for assessing photoreceptor function and neural responses. Advantages of this technique include non-invasiveness, and objective evaluation of retinal function on a layer-by-layer basis. In brief, the flash ERG is assessed in a dark adapted eye. The initial a-wave (initial negative deflection) is primarily derived from photoreceptors where the second half of the a-wave is a combination of photoreceptors, bipolar, amacrine, and Muller cells. The b-wave (positive deflection) originates in retinal cells that are post-synaptic to the photoreceptors and are used as a readout for photoreceptor function. Spectral domain optical coherence tomography (SD-OCT) is also used for detailed and non-invasive evaluation of the retinal architecture in vivo. SD-OCT accurately reflects retinal morphological changes that occur during retinal disease progression, including retinal detachment.

Other methods for assessing vision include standard eye examinations that are known in the art. For example, a Snellen chart, or variations thereof, containing letters and/or numbers is used to determine visual acuity. Decreased ability to distinguish and recognize the letters and/or numbers vision loss or acuity. An increased ability to distinguish and recognize the letters and/or numbers after treatment indicates efficaciousness of the treatment, or regeneration of retinal cells. Additional methods for assessing vision include visual field assessment and optokinectic assay The subject is a mammal in need of such treatment, e.g., a subject that has been diagnosed with an ocular injury or disease associated with vision loss, retinal cell damage, or retinal degeneration. The subject has an injured or diseased eye. For example, the subject suffers from photoreceptor degeneration. The mammal is, e.g., a human, a primate, a mouse, a rat, a dog, a cat, a horse, as well as livestock or animals grown for food consumption, e.g., cattle, sheep, pigs, chickens, and goats. Preferably, the mammal is a human.

Ocular injuries or diseases that are treated using the compositions described herein are associated with retinal damage and/or retinal degeneration. The ocular injuries or diseases may result in vision loss. Examples of such injuries or diseases include macular degeneration, diabetic retinopathy, retinitis pigmentosa, cone dystrophy geographic atrophy, detachment ischemia, optic nerve neuritis, ocular cancer, glaucoma, retinal trauma, physical trauma to the optic nerve and surrounding tissues, or retinal nerve damage.

The compositions described herein are administered topically, intraocularly, intravitreally, subretinally, or subconjuntivally. Preferably, the compositions described herein are administered intravitreal injection or subretinal injection. The composition is administered at a dosage of 1-50 mg/ml or 0.1-350 µM. Preferably, the dosage is less than 75 mg/ml or 500 µM. Dosages greater than 75 mg/ml or 500 µM result in cytotoxicity.

The composition is administered at least once. In one embodiment, the composition is administered twice, three times, four times, five times, six times, seven times, eight times, nine times or ten times in one treatment period. The treatment period may be 1 day, 2 days, 3 days, 4 days, 5 days, 6 days, 1 week, 2 weeks, 3 weeks, 4 weeks, 5 weeks, 6 weeks, 7 weeks, or 8 weeks. In another embodiment, the composition is administered once every 3 to 5 days in a treatment period. In some embodiments, the subject may be administered the composition over more than one treatment period.

In one embodiment, the composition is administered before retinal cell transplantation. For example, the composition is administered at least 1 hour, 2 hours, 4 hours, 6 hours, 12 hours, 16 hours, 1 day, 2 days, 3 days, 4 days, 5 days, 6 days, or 1 week before transplantation.

The composition further comprises a pharmaceutically acceptable carrier and/or ophthalmic excipient. Exemplary pharmaceutically acceptable carrier include a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

All compounds of the invention are purified and/or isolated. Specifically, as used herein, an "isolated" or "purified" small molecule, nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. Purified also defines a degree of sterility that is safe for administration to a human subject, e.g., lacking infectious or toxic agents.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to enhance or restore vision, or increase photoreceptor activity. Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below.

All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIGS. 1A-C show GFAP immunolabelling in retinal flat-mounts at 3 (FIGS. 1A and 1B) and 10 (FIG. 1C) days after saline (FIG. 1Aa) or α-AA (FIGS. 1A and 1B) subretinal injection. Note that pretreatment with α-AA resulted in temporary elimination of GFAP expression around the injected area at day 3 post injection (FIG. 1B) that was recovered by day 10 post α-AA injection (FIG. 1C). Arrows point to the injection site. Scale bars, 40 μm. (FIG. 1D) Representative western blot of triplicate experiments examining GFAP expression in normal (N), saline- (S) or α-AA (A)-injected retinas. Retinal proteins were collected at days 3 and 7 post injection. Note the reduced GFAP expression in 3 day α-AA (A), but not saline (S)-injected retinas, when are compared to controls; moreover, by day 7 post injection no significant difference of GFAP levels was detected between the saline- and α-AA-treated groups. No neuronal toxicity was noted.

FIGS. 2A-2H show fluorescent staining images demonstrating that normal retinal lamina structure and neuronal morphology in α-AA treated retina. Photomicrographs of retinal sections taken at day 3 after saline (FIGS. 2A-D) or α-AA (FIGS. 2E-H) injection that were stained by Nissl (FIGS. 2A,E) or a primary antibody against photoreceptor marker recoverin (green; B,C,F,G) or amacrine neuron marker syntaxin (green; FIGS. 2D,H). No significant difference in retinal laminal architecture or expression of photoreceptor or amacrine cell markers was noted in α-AA-injected retinas. Arrows point to the injection sites. GCL, ganglion cell layer; INL, inner nuclear layer; ONL, outer nuclear layer. Scale bar, 40 μm.

(FIGS. 3A and 3B) Representative photomicrographs of retinal flat-mounts showing repopulated GFP+ cells in saline- (FIG. 3A) and α-AA-treated (FIG. 3B) retinas at 21 days post transplantation. FIG. 3C shows a graph quantifying grafted cells that repopulated into the normal (N; black bar), saline- (S; dashed bar) and α-AA (A; white bar)-treated retinas. (FIG. 3D) Percentages of α-AA- (A), saline-treated (S), or non-treated (N) cells that extended neurites longer than 1 (>1×) or 3 (>3×) cell body lengths into the host retina (n=9/group). Data represent mean±S.D. *P<0.05, ***P<0.001 by ANOVA or two-tailed student t test as compared to the saline-treated group.

FIGS. 4A-K show fluorescent staining images demonstrating that integration and differentiation of cells engrafted into the α-AA treated retinas. FIGS. 4A-C show epifluorescent photomicrographs of retinal sections taken at day 1 post transplantation that were immunolabeled with primary antibody against neural progenitor cell marker nestin. Note that most GFP+ cells (green; FIG. 4A) were colocalized with anti-nestin immunolabelling (red; FIGS. 4B,C). FIGS. 4D-K are images of retinal sections taken at 21 days post transplantation were immunolabeled for retinal glial cell marker GFAP (red; FIGS. 4E-G) or retinal ganglion cell maker brn-3b (red; FIGS. 4I-K). Note that grafted GFP+ cells integrated into the GCL of the host retina differentiated into astrocytes and retinal ganglion cells, similar to the types of host cells resided in the same layer of the retina. FIGS. 4G and 4K show the inserts of FIGS. 4F and 4J, respectively. Scale bars, 40 μm.

FIGS. 5A-J show fluorescent staining images demonstrating that generation of new photoreceptors by transplanted progenitor cells. FIGS. 5A-F shows representative epifluorescence photomicrographs of retinal sections taken at 21 days post transplantation that were immunolabeled with primary antibody against rhodopsin (red; FIGS. 5B-F) or cone-opsin (red; FIGS. 5I and 5J). Note transplanted cells that integrated into the ONL reveal characteristic mature photoreceptor cell morphology with differentiated outer segment structures and colocalization with rhodopsin (FIGS. 5A-F) or cone-opsin (FIGS. 5G-J). FIGS. 5D-F show higher magnification of FIGS. 5A-C. Scale bars: 40 μm (FIGS. 5A-C), 8 μm (FIGS. 5D-F), 16 μm (FIGS. 5G-J).

FIGS. 6A-C show fluorescent staining images and a graph of the resultant quantification of rod and cone differentiation by transplanted cells integrated into the ONL. FIGS. 6A and B show epifluorescence photomicrographs of orthogonal projection of retinal sections that were immunolabeled by anti-rhodopsin (FIG. 6A) or anti-cone-opsin (FIG. 6B). FIG. 6C is a graph showing the percentage of integrated cells expressing rhodopsin or cone-opsin (n=4).

FIGS. 8A-K show fluorescent staining images demonstrating the integration and differentiation of transplanted cells in the retina of Gnat1$^{-/-}$ mice. FIGS. 8A-K show that GFP+ cells integrated into the INL of Gnat1$^{-/-}$ mice exhibited the morphology of amacrine cells and expressed amacrine cell marker syntaxin (red). FIGS. 8E-L show that grafted cells integrated into the ONL of Gnat1$^{-/-}$ mice expressed photoreceptor cell specific marker, recoverin (red; FIGS. 8F-H) and rod photoreceptor cell marker, rhodopsin (red; FIGS. 8J-L). Scale bars, 40 μm (FIGS. 8A and 8B), 16 μm (FIGS. 8C, 8E-G and 8I-K), 8 μm (FIGS. 8D, 8H, 8L).

FIGS. 9A-I show fluorescent staining images and a graph demonstrating the formation of synaptic connections and functional integration in to the host by transplanted cells. FIGS. 9A-D show grafted cells integrated into the ONL extended neurites that reached the outer plexiform layer OPL and developed bossom-like structures (FIG. 9A) that were colocalized with postsynaptic bipolar cell marker PKCα (FIG. 9C) or presynaptic marker synpatophysin (FIGS. 9D, E, G, H). Scale bars, 16 μm (FIGS. 9A-C and 9E-G), 8 μm (FIGS. 9D and 9H). FIG. 9I is a graph of the quantification of ERG a-wave amplitudes from wild-type without receiving retinal engraftment and from Gnat1$^{-/-}$ (Gnat$^{-/-}$) mice with or without retinal engraftment (n=5/group). The host retinas received no pretreatment or treatment (pre-trt) with either saline or α-AA. Data represent mean±S.D. **P<0.005 over that of the untreated Gnat1$^{-/-}$ mouse group by ANOVA.

FIG. 10A shows an image of immunofluorescence performed on retinal sections. Proliferation markers, such as BrdU and phospho-histone H3 (pHisH3) were stained and overlayed to show proliferation of the Muller cells in the retina. FIG. 10B shows a graph quantifying the percentage of proliferating Muller cells from the immunofluorescence studies comparing saline (control) to varying increasing concentrations of αAA.

FIGS. 11A-H show fluorescent staining images demonstrating that Muller cells trans-differentiate into retinal progenitors upon α-AA stimulation Immunofluorescence was performed on retinal sections. FIG. 11A is an image of a cells stained with a marker for Nestin, a Muller cell marker. FIGS. 11B and 11E are an images of cells stained with a marker for BrdU, a proliferation marker. FIG. 11C shows an overlay of the markers shown in FIGS. 11A and 11B that was used to identify proliferating Muller cells. FIG. 11F shows an image of cells stained with Chx10, a retinal progenitor marker. FIG. 11G shows an overly of images from FIGS. 11E and 11F showing Müller cells that had trans-differentiated to retinal progenitor cells (overlay). FIGS. 11D and 11H are increased magnification images of FIGS. 11C and 11G respectively.

FIGS. 12A-H show fluorescent staining images demonstrating that α-AA treatment leads to generation of new photoreceptors. Double-immunofluorescence labeling of BrdU and photoreceptor cell marker, Nr2e3 (FIGS. 12A-D) or rhodopsin (FIGS. 12E-H), was performed on retinal sections taken from mice at 7 days (FIGS. 12A-D) and 21 days (FIGS. 12E-H) after αAA injection.

FIGS. 13A-E show images of electron micropy and a western blot demonstrating transient loss of GFAP expression after α-AA stimulation. Representative photomicrographs of electron microscopy of retinal sections taken from mice at 3 days post injection of either saline (cont; FIGS. 13A and 13B) or α-AA (FIGS. 13C and 13D). Arrows and arrow heads mark the Müller cells. FIG. 13E shows an image of a western blot analysis confirming transient GFAP protein level changes at 3 and 7 days after saline (S) or α-AA (A) administration.

FIGS. 14A-E shows images of electroretinography (ERG) and bar graphs demonstrating that α-AA rescues cone photoreceptor function in Rho$^{-/-}$ mice. FIGS. 14A and 14B show representative ERG recording at 3 Hz and 10 Hz flickers from 10 week old Rho$^{-/-}$ mice that received either saline (control) or α-AA treatment at 6 week-old. FIGS. 14C and 14D show the quantification of the ERG b-wave amplitudes. FIG. 14E is a cartoon of a mouse.

FIGS. 15A-D show light induced spike histograms and epifluorescence photomicrographs demonstrating that α-AA restores light induced response in the retina of Rho$^{-/-}$ mice. FIGS. 15A and 15B show light induced spike histograms measured via cell-attached patch clamp from RGCs of 11 week-old Rho$^{-/-}$ mice that received saline (FIG. 15A) or α-AA injection (FIG. 15B). A 300 μm flash was presented for the 1 second interval indicated by the boxes. FIGS. 15C and 15D show representative epifluorescence photomicrographs of retinal sections taken from 11 week-old Rho$^{-/-}$ mice that received a single subretinal injection of saline (FIG. 15C) or αAA (FIG. 15D) at 6 week-old. Retinal sections were double-labeled with nuclear marker DAPI and primary antibody against cone opsin. INL, inner nuclear layer. ONL, outer nuclear layer.

DETAILED DESCRIPTION

Figures 1A, 1B, 1C, 1D:
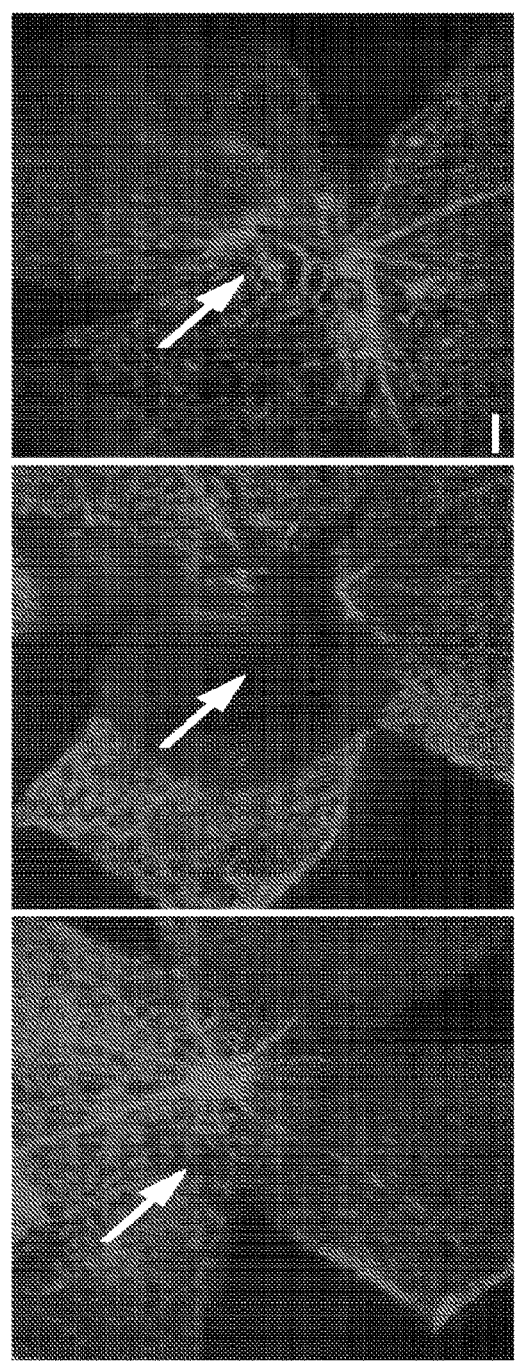
FIGS. 1A-D show images of fluorescent staining and a western blot demonstrating that α-AA transiently disrupts retinal glial structure without adverse effect on retinal neurons.

Neurons in the mammalian central nervous system (CNS), including the retina, regenerate poorly or not at all after injury. As a result, retinal injury or disease leads to permanent loss of function or blindness. Retinal degenerative disorders, such as retinitis pigmentosa and age-related macular degeneration, are leading causes of blindness. Currently, no effective therapies are available that can reverse vision loss due to retinal injury or diseases.

A previous study demonstrated that alpha-aminoadipate (α-AA) can stimulate Muller cell proliferation in the retina and proliferating Muller cells can differentiate into photoreceptor cells and Muller glia (Takeda et al., Invest Ophtalmol Vis Sci, 2009, 49(3):1142-1150; hereby incorporated by reference in its entirety). However, proliferation and increased numbers of photoreceptor cells does not predictably result in any change in or enhancement of visual response or visual restoration. Moreover, these results were only performed in wild-type mice with normal, or undamaged, retinas.

It is known in the art that the environment and signaling pathways of diseased or injured retinas are completely different from that of normal retinas. Diseased or injured retinas have been shown to produce anti-regenerative signals and generate a hostile environment that prevents regeneration, integration and neural differentiation of progenitor cells either derived from an endogenous source or via transplantation. As such, therapeutic treatments that show some efficacy in normal retinas cannot be predicted to demonstrate equivalent success or efficacy in injured or diseased retinas.

Muller cells are active players in both normal retinal function and in retinal injury and disease (Bringmann et al., Progress in Retinal and Eye Research, 2009, 28:423-451). Reactive Muller cells have protective functions by releasing antioxidants and neurotrophic factors, and may contribute to retinal regeneration by generating neural progenitor/stem cells in response to damage. However, Muller cell gliosis has also been shown to contribute to neurodegeneration and impede regenerative processes in the retinal tissue by the formation of glial scars. Muller cells can release proinflammatory cytokines, such as TNF, and monocyte chemoattractant protein (MCP)-1 (Ccl-2). Muller cells can also produce excess nitric oxide and free nitrogen radicals that have toxic effects on surrounding neurons. Thus, increased proliferation of Muller cells can lead to detrimental or anti-degenerative effects in an injured or diseased retina.

Injured and diseased retinas also develop glial scars, which prevent neuronal regeneration and impede repair in damaged and injured retinas by generating a physical barrier to neuronal growth. Furthermore, cells in the glial scar, such as astrocytes and/or other retinal neurons, secrete growth-inhibitory molecules that chemically prevent neuronal growth and/or axon extensions. Muller cell proliferation has also been shown to contribute to glial scar formation, Although retinal regeneration has been successfully demonstrated in injured or diseased retinas in the zebrafish model system, zebrafish retinas do not form glial scars. Thus, results derived from the zebrafish model cannot be faithfully extrapolated to mammalian eyes with predictable results, or expectation of success.

In contrast to the prior art, the methods and compositions provided herein demonstrate unexpected and superior results in enhancing and restoring vision in diseased and injured eyes of subjects suffering from retinal damage or degeneration. Specifically, the effects of administration of alpha-aminoadipate were observed in Rho−/− mice, which exhibit degeneration of photoreceptor cells (rod and cone photoreceptor cell death). Photoreceptor cell death is measured or assessed by electroretinography, and a reduction or absence of α-wave and/or b-waves. The progression and pathology observed in the diseased retinas of Rho−/− mice are closely recapitulate that of human retinitis pigmentosa, and thus this mouse model is an art-accepted model for human retinal degenerative diseases. Administration of αAA directly to the diseased eyes of the Rho−/− mice resulted in proliferation of Muller cells. Furthermore, proliferating Muller cells were also shown to be capable of trans-differentiating into retinal progenitor cells (expressing retinal progenitor markers). Measurement of photoreceptor activity shows an increase in a and b-waves by ERG analysis and patch clamp recordings, when compared to saline-injected control diseased eyes. Thus, the present disclosure demonstrates unexpected and superior results, particularly in the unpredictable environment of diseased retinas, in comparison to the results obtained in previous from normal retinas or models that do not faithfully recapitulate mammalian diseased retinas.

The methods described herein provide advantages over transplantation methods, by stimulating endogenous retinal cells to proliferate and differentiate into stem/progenitor cells, thereby regenerating new cells endogenously. These advantages include the independence from shortages of donor cells, prevention of any disease, disorders, or complications resulting from transplantation, and prevention of immune rejection. Furthermore, there is evidence that endogenously regenerated neurons can readily breach the glial barrier and are better programmed to integrate into the neuro-circuitry compared to the transplanted cells.

The methods and compositions provided herein are also useful for enhancing the efficacy of retinal cell replacement therapy by transiently breaking down the host barrier to grafted cell integration. Administration of α-AA disrupts residential glial structures that allows the proper differentiation and establishment of functional connectivity of transplanted retinal cells with the host, and promoted robust grafted cell incorporation and restoration of rod photoreceptor activity. Furthermore, application of α-AA did not cause adverse effect on general retina structure and their neurons, demonstrating the safety for use in the retina.

Analogs of alpha-aminoadipate comprise those with the following formula II:

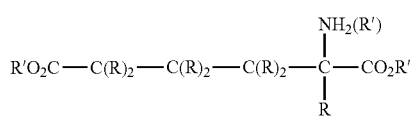

wherein, independently for each occurrence,

R represents H, alkyl, or aryl;

and R' is absent or represents H.

Alpha-aminoadipate has the following formula II:

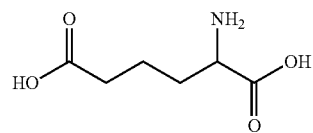

Also included are pharmaceutically acceptable addition salts of analogs of formula I or II. Also included are prodrugs of the α-AA or analogs of formula I or II. Prodrugs are considered to be any covalently bonded carriers which release the active parent drug in vivo.

Furthermore, functional analogs of α-AA may include glutamate, glutamate agonists, aspartate, homocysteate, N-methyl D-aspartate (NMDA), L-ibotenate, and D-ibotenate.

Glutamate has the following formula III:

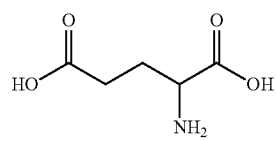

Aspartate has the following formulate IV:

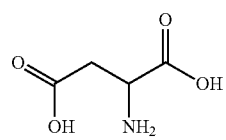

Homocysteate has the following formula V:

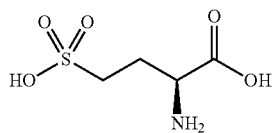

N-methyl D-aspartate (NMDA) has the following formula VI:

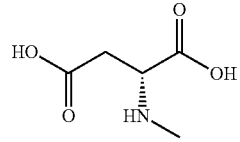

Ibotenate has the following formula VII:

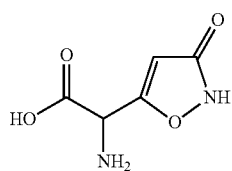

(VII)

Ibotenate has L and D isomers, both of which may be functional analogs of α-AA.

For administration to a subject such as a human or other mammal (e.g., companion, zoological or livestock animal), an agent that increases photoreceptor activity is desirably formulated into a pharmaceutical composition containing the active agent in admixture with one or more pharmaceutically acceptable diluents, excipients or carriers. Examples of such suitable excipients for can be found in U.S. Publication 2009/0298785 (incorporated by reference herein in its entirety), the *Handbook of Pharmaceutical Excipients,* 2nd Edition (1994), Wade and Weller, eds. Acceptable carriers or diluents for therapeutic use are well-known in the pharmaceutical art, and are described, for example, in *Remington: The Science and Practice of Pharmacy,* 20th Edition (2000) Alfonso R. Ciennaro, ed., Lippincott Williams & Wilkins: Philadelphia, Pa. Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the e intended route of administration and standard pharmaceutical practice. The pharmaceutical composition can contain as, or in addition to the carrier, excipient or diluent any buffering agent(s), suitable binder(s), lubricant(s), suspending agent(s), coating agent(s), agent(s), isotonifier(s), non-ionic detergent(s), and other miscellaneous additives. Such additives must be non-toxic to the recipients at the dosages and concentrations employed.

Buffering agents help to maintain the pI-1 in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodiurri citrate mixture, citric acid-monosodium citrate mixture, etc.), succinate buffers (e.g., succinic acid-monosodium succinate mixture, succinic acid-sodium hydroxide mixture, succinic acid-disoclium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Examples of suitable binders include starch, gelatin, natural sugars such as glucose, anhydrous lactose, free-flow lactose, β-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents can be provided in the pharmaceutical composition. Examples of preservatives include sodium benzoate, sorbic acid and esters of p-hydroxybenzoic acid. Antioxidants and suspending agents can be also used. Preservatives may be added to retard microbial growth, and may be added in amounts ranging from 0.2-1% (w/v), Suitable preservatives for use with the present invention include phenol, benzyl alcohol, meta-cresol, methyl paraben, propyl paraben, octadecyldimethyibenzyl ammonium chloride, benzalconium halides (e.g., chloride, bromide, iodide), hexamethonium chloride, alkyl parabens such as methyl propyl paraben, catechol, resorcinol, cyclohexanol, and 3-pentanol.

Isotonicifiers sometimes known as "stabilizers" may be added to ensure isotonicity of liquid compositions of the present invention and include polyhydric sugar alcohols, preferably trihydric or higher sugar alcohols, such as glycerin, erythritol, arabitol, xylitol, sorbitol and mannitol.

Stabilizers refer to a broad category of excipients which can range in function from a hulking agent to an additive which solubilizes the therapeutic agent or helps to prevent denaturation or adherence to the container wall, Typical stabilizers can be polyhydric sugar alcohols (enumerated above); amino acids such as arginine, lysine, glycine, glutamine, asparagine, histidine, alanine, ornithine, L-leucine, 2-phenylalanine, giutamic acid, threonine, etc organic sugars or sugar alcohols, such as lactose, trehalose, stachyose, mannitol, sorbitol, xylitol, ribitol, myoinisitol galactitol, glycerol and the like, including cyclitols such as inositol; polyethylene glycol; amino acid polymers; sulfur containing reducing agents, such as urea, glutathione, thioctic acid, sodium thioglycolate, thioglycerol, .alpha.-monothioglycerol and sodium thio sulfate; low molecular weight polypeptides (<10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions, Such techniques are disclosed in Remington's Pharmaceutical Sciences, 16th edition, A. Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody variant, which matrices are in the form of shaped articles, e.g., films, or microcapsules. Examples of sustained-release matrices include polyesters, hydrogels (for example, poly(2-hydroxyethyl-methacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The active ingredients may also be entrapped in microcapsule prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the anti-complement inhibitors, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

A suitable formulation of the compositions disclosed herein is a hydrogel. A hydrogel is a colloidal gel formed as a dispersion in water or other aqueous medium. Thus a hydrogel is formed upon formation of a colloid in which a dispersed phase (the polymer) has combined with a continuous phase (i.e. water) to produce a viscous jellylike product; for example, coagulated silicic acid. A hydrogel is a three-dimensional network of hydrophilic polymer chains that are crosslinked through either chemical or physical bonding. Because of the hydrophilic nature of the polymer chains, hydrogels absorb water and swell (unless they have already absorbed their maximum amount of water). The swelling process is the same as the dissolution of non-crosslinked hydrophilic polymers. By definition, water constitutes at least 10% of the total weight (or volume) of a hydrogel.

Examples of hydrogels include synthetic polymers such as polyhydroxy ethyl methacrylate, and chemically or physically crosslinked polyvinyl alcohol, polyacrylamide, poly(N-vinyl pyrolidone), polyethylene oxide, and hydrolysed polyacrylonitrile. Examples of hydrogels which are organic polymers include covalent or ionically crosslinked polysaccharide-based hydrogels such as the polyvalent metal salts of alginate, pectin, carboxymethyl cellulose, heparin, hyaluronate and hydrogels from chitin, chitosan, gellan and xanthan. The particular hydrogels used in our experiment were a cellulose compound (i.e. hydroxypropylmethylcellulose [HPMC]) and a high molecular weight hyaluronic acid (HA).

A drug delivery system within the scope of the present invention can be formulated with particles of an active agent dispersed within a biodegradable polymer. Release of the active agent is achieved by erosion of the biodegradable polymer matrix and by diffusion of the particulate agent into an ocular fluid, e.g., the vitreous, with subsequent dissolution of the polymer matrix and release of the active agent. Factors which influence the release kinetics of active agent from the implant can include such characteristics as the size and shape of the implant, the size of the active agent particles, the solubility of the active agent, the ratio of active agent to polymer(s), the method of manufacture, the surface area exposed, the density of the implant and the erosion rate of the polymer(s).

The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the drug delivery system.

Biodegradable polymers which can be used include, but are not limited to, nanoparticles and polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked.

Polylactide (PLA) polymers exist in 2 chemical forms, poly(L-lactide) and poly(D,L-lactide). The pure poly(L-lactide) is regioregular and therefore is also highly crystalline, therefore degrades in vivo at a very slow rate. The poly(D,L-lactide) is regiorandom which leads to more rapid degradation in vivo. Therefore a PLA polymer which is a mixture of predominantly poly(L-lactide) polymer, the remainder being a poly(D-lactide) polymer will degrade in vivo at a rate slower that a PLA polymer which is predominantly poly(D-lactide) polymer. A PLGA is a co-polymer that combines poly(D,L-lactide) with poly(glycolide) in various possible ratios. The higher the glycolide content in a PLGA the faster the polymer degradation.

The release rate of the active agent can depend at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release. The release rate of the active agent can also be influenced by the crystallinity of the active agent, the pH in the implant and the pH at interfaces.

The release kinetics of the drug delivery systems of the present invention can be dependent in part on the surface area of the drug delivery systems. A larger surface area exposes more polymer and active agent to ocular fluid, causing faster erosion of the polymer and dissolution of the active agent particles in the fluid.

The drug delivery systems my include a therapeutic agent mixed with or dispersed within a biodegradable polymer. The drug delivery systems compositions can vary according to the preferred drug release profile, the particular active agent used, the ocular condition being treated, and the medical history of the patient, Therapeutic agents which can be used in our drug delivery systems include, but are not limited to (either by itself in a drug delivery system within the scope of the present invention or in combination with another therapeutic agent): ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, methicillin; lincosamides such as lincomycin; polypeptide antibiotics such as polymixin and bacitracin; tetracyclines such as tetracycline; quinolones such as ciproflaxin, etc.; sulfonamides such as chloramine T; and sulfones such as sulfanilic acid as the hydrophilic entity, anti-viral drugs, e.g. acyclovir, gancyclovir, vidarabine, azidothymidine, azathioprine, dideoxyinosine, dideoxycytosine, dexamethasone, ciproflaxin, water soluble antibiotics, such as acyclovir, gancyclovir, vidarabine, azidothymidine, dideoxyinosine, dideoxycytosine; epinephrine; isoflurphate; adriamycin; Neomycin; mitomycin; ara-C; actinomycin D; scopolamine; and the like, analgesics, such as codeine, morphine, keterolac, naproxen, etc., an anesthetic, e.g. lidocaine; β-adrenergic blocker or β-adrenergic agonist, e.g. ephidrine, epinephrine, etc.; aldose reductase inhibitor, e.g. epairestat, ponalrestat, sorbinil, tolrestat; antiallergic, e.g. cromolyn, beclomethasone, dexamethasone, and flunisolide; colchicine, anthelminthic agents, e.g. ivermectin and suramin sodium; antiamebic agents, e.g. chloroquine and chlortetracycline; and antifungal agents, e.g. amphotericin, etc., anti-angiogenesis compounds such as anecortave acetate, retinoids such as Tazarotene, anti-glaucoma agents, such as brimonidine (Alphagan and Alphagan P), acetozolamide, bimatoprost (Lumigan), timolol, mebefunolol; memantine, latanoprost (Xalatan); alpha-2 adrenergic receptor agonists; 2-methoxyestradiol; anti-neoplastics, such as vinblastine, vincristine, interferons; alpha, beta and gamma, antimetabolites, such as folic acid analogs, purine analogs, and pyrimidine analogs; immunosuppressants such as azathiprine, cyclosporine and mizoribine; miotic agents, such as carbachol, mydriatic agents such as atropine, protease inhibitors such as aprotinin, camostat, gabexate, vasodilators such as bradykinin, and various growth factors, such epidermal growth factor, basic fibroblast growth factor, nerve growth factors, carbonic anhydrase inhibitors, and the like.

Pharmaceutical compositions comprising alpha-aminoadipate or a functional analog thereof may be prepared for storage as a lyophilized formulation or aqueous solution by mixing the polypeptide having the desired degree of purity with optional pharmaceutically-acceptable carriers, excipients, or stabilizers typically employed in the art.

The composition should contain a sufficient amount of active ingredient to achieve the desired effect (referred to herein as the "effective amount" as can be readily determined by workers skilled in the art. In general, the solubility of the active ingredient in water and the concentration of the active ingredient needed in the tissue, guide the amount and rate of release of the agent. Compositions for systemic administration require a different "effective amount" compared to compositions for direct injection into the eye or retina.

A person of ordinary skill in the art can readily determine an appropriate dosage to administer to a subject without undue experimentation. Typically, a physician determines the actual dosage that will be most suitable for an individual subject based upon a variety of factors including the activity of the specific compound employed, the metabolic stability and length of action of the compound, the age, body weight, general health, diet, mode and time of administration, rate of excretion, drug combination, the severity of the particular condition, and the individual undergoing therapy. To determine a suitable dose, the physician or veterinarian could start doses levels lower than that required in order to achieve the desired therapeutic effect and gradually increase the dosage until the desired effect is achieved. Similarly, the number of administrations of the compositions described herein to achieve the desired effect may also be determined without undue experimentation. This is considered to be within the skill of the artisan and one can review the existing literature on a specific agent to determine optimal dosing.

In some embodiments, the composition is administered in the form of a liquid (e.g., drop or spray) or gel suspension. Alternatively, the composition is applied to the eye via liposomes or infused into the tear film via a pump-catheter system. Further embodiments embrace a continuous or selective-release device, for example, membranes such as, but not limited to, those employed in the OCUSERT System (Alza Corp., Palo Alto, Calif.) In an alternative embodiment, the p53 activator is contained within, carried by, or attached to a contact lens, which is placed on the eye. Still other embodiments embrace the use of the composition within a swab or sponge, which is applied to the ocular surface.

In some cases, the composition further comprises a pharmaceutically acceptable carrier, e.g., a pharmaceutically acceptable salt. Suitable ocular formulation excipients include FDA approved ophthalmic excipients, e.g., emulsions, solutions, solution drops, suspensions, and suspension drops. Other suitable classifications include gels, ointments, and inserts/implants.

Exemplary excipients for use in optimizing ocular formulations include alcohol, castor oil, glycerin, polyoxyl 35 castor oil, Tyloxapol, polyethylene glycol 8000 (PEG-8000), ethanol, glycerin, cremaphor, propylene glycol (pG), polypropylene glycol (ppG), and polysorbate 80. In some cases, citrate buffer and sodium hydroxide are included to adjust pH.

Preferably, the compositions are delivered by topical, intravitreal, intraocular, subretinal, or systemic administration. For example, the compositions are administered by intraocular injection or subretinal injection. The compositions may also be delivered systemically. Antibodies have been previously shown to be successfully administered and delivered via systemic delivery, such as anti-C5 antibody for the treatment of wet age-related macular degeneration (AMD). Although systemic administration of an anti-immune response therapeutic may have adverse side effects, such as increased occurrence of infections, there has been no evidence to date that shows that systemic administration of anti-C5 antibody caused sufficient suppression of the immune system to increase occurrence of infections.

As described in detail below, application of alpha-aminoadipate ($\alpha$-AA), a glutamate analogue that selectively binds astroglial cells, ameliorates the transplantation barrier and permits functional integration by grafted retinal progenitors. $\alpha$-AA was pre-injected into the subretinal space of the wild-type mice or mice lacking the $\alpha$-subunit transducin (Gnat1$^{-/-}$) 2 days before transplantation. Two days later, retinal progenitor cells were isolated from neonatal mice expressing an enhanced green fluorescent protein transgene driven by a chicken $\beta$-actin promoter and cytomegalovirus enhancer and injected subretinally. Transplanted progenitor cells stayed clustered at the injection site and failed to incorporate into the untreated or saline-treated retina. In contrast, pretreatment with $\alpha$-AA resulted in photoreceptor differentiation and robust grafted cell integration into the outer nuclear layer. Differentiated photoreceptor cells revealed typical morphology of inner and outer segments and synaptic bossoms that were connected with the appropriate retinal layers. Moreover, pretreatment with $\alpha$-AA resulted in restoration of light-induced rod responses and recovery of electroretinograms following transplantation in Gnat1$^{-/-}$ mice, which carry inherited rod photoreceptor dysfunction. $\alpha$-AA effectively eliminates the glial barrier to retinal transplantation that allows photoreceptor differentiation of progenitor cells and functional restoration following transplantation in the diseased retina.

Also described below are the effects of administration of alpha-aminoadipate in Rho$^{-/-}$ mice, which exhibit degeneration of photoreceptor cells (rod and cone photoreceptor cell death). Photoreceptor cell death can be measured or assessed by electroretinography, and a reduction or absence of a-wave and/or b-waves. Administration of $\alpha$AA directly to the diseased eyes of the Rho$^{-/-}$ mice resulted in proliferation of Muller cells. Furthermore, proliferating Muller cells were also shown to be capable of trans-differentiating into retinal progenitor cells (expressing retinal progenitor markers). Measurement of photoreceptor activity shows an increase in a and b-waves by ERG analysis and patch clamp recordings, when compared to saline-injected control diseased eyes.

The following materials and methods were used to generate the data described herein.

Animals

Adult B6/129SF2 and C57BL/6J wild-type, Gnat1$^{-/-}$, Rho$^{-/-}$ and enhanced green fluorescent protein (EGFP) transgenic mice were maintained using standard protocols. These mice carry a similar B6/129 or B6 genetic background.

Immunohistochemistry

Mice were anesthetized by intraperitoneal injection of ketamine (62.5 mg/kg) and xylazine (12.5 mg/kg) and transcardially perfused with phosphate buffered saline (PBS) followed by 4% paraformaldehyde in PBS. Retinal flat-mounts or transverse retinal sections (14 µm) were preblocked with PBS containing 3% bovine serum albumin (Sigma-Aldrich, St. Louis, Mo.) and 0.3% Triton X (Sigma-Aldrich) and incubated, first, with primary antibody overnight, and then with secondary antibody for 1 hour at room temperature. The following antibodies were used: Cy3-conjugated monoclonal antibody against GFAP (1:1000; Sigma), Brn-3b (1:200; Santa Cruz Biotechnology; Santa Cruz, Calif.), mouse anti-rodopsin (1:4000; Rho1D4), chick anti-cone-opsin (1:300), and Cy-2, Cy-3 or Cy-5-conjugated secondary antibody (Jackson ImmunoResearch; West Grove, Pa.). Assessment of morphological integration were quantified by counting EGFP+ cells located outside of transplanted cell clusters in retinal whole-mounts. Statistical significance was determined by either the two tailed student t test or ANOVA.

Western Blot Analysis

To determine the effect of $\alpha$-AA on retinal glial cells, mouse retinas were dissected and homogenized in lysis buffer 3% sodium dodecyl sulfate (Sigma-Aldrich), 0.3 M sucrose (Sigma-Aldrich), 1 mM orthovanadium (Sigma-Aldrich)]. Protein concentrations were determined with a BCA assay (Pierce; Rockford, Ill.). Protein (20 µg) was loaded on a 10% sodium dodecyl sulfatepolyacrylamide gel and transferred to a nitrocellulose membrane. The blot was blocked in 1% bovine serum albumin (Sigma-Aldrich) and 4% dry milk in PBS and probed with primary antibodies against GFAP (1:1000; Chemicon; Temecula, Calif.) and $\beta$-actin (Sigma-Aldrich) as loading controls. After incubation with appropriate secondary antibodies conjugated to horseradish peroxidase (Jackson Immunochemicals; West Grove, Pa.), detection was performed with Super Signal West Pico (Pierce).

Electron Microscopy

Mice were sacrificed 3 days after receiving the injection of $\alpha$-AA (1 µg/µl) or saline as controls by injection of overdose of ketamine/xylazine followed by cervical dislocation, and the eyeballs were dissected, fixed with Karnovsky's fixative (pH 7.4) for 24 h. The quadrants of the eyes that received subretinal injection were dissected and embedded in Epon-Araldite. Semi-thin sections (1-2 µm) were stained with phenylenediamine phase staining. The sections were examined and photographed with a transmission electron microscope (EM410; Philips; Eindhoven, The Netherlands). Ten randomly selected retinal sections of each eye were photographed at 1900× magnification, and all Müller glial nuclei in the photomicrograph were counted.

Retinal Transplantation

At 2 days before transplantation, 2 µl of a solution containing either α-AA (1 µg/µl) or saline (control) was injected unilaterally into the subretinal space of recipient wild-type or Gnat1$^{-/-}$ mice (>2 months old). The procedure for donor cell preparation was essentially as described by Kinouchi et al, 2003, Nat Neurosci, 6:863-868. Briefly, retinal progenitor cells were isolated from postnatal day 0 (P0) EGFP transgenic mice. Cell suspensions containing approximately 1×10$^6$ dissociated cells were injected slowly through a glass micropipette into the subretinal space of pretreated recipient mice through the same injection site where either saline or α-AA had been injected 2 days prior.

Electroretinography (ERG)

At 21 days post transplantation, Gnat1$^{-/-}$ mice that had received either α-AA or saline-pretreatment followed by retinal progenitor cell transplantation were analyzed by full-field ERG. Mice were dark adapted for 12 hours and then anesthetized by intraperitoneal injection of ketamine (62.5 mg/kg) and xylazine (12.5 mg/kg). The pupils were dilated with 1% tropicamide (Falcon Pharmaceuticals; Fort Worth, Tex.) and 1% cyclopentolate hydrochloride (Akorn; Buffalo Grove, Ill.) eye drops in dim red light. A 0.25-mm gold-wire electrode (Alfa Aesar; Ward Hill, Mass.) was placed on the center of the mouse cornea and connected to a visual electrodiagnostic system (EPIC-2000; LKC Technologies, Gaithersburg, Md.). Scotopic ERGs, which measure primarily rod function, were elicited with 10-msec flashes of white light at 15 dB, with 60-second delays between flashes. A total of six scans were taken and averaged; the a-wave amplitudes were measured from baseline to the peak in the cornea-negative direction. The results from each group of mice were averaged, and the means of the α-AA treated and contralateral control eyes were compared. Statistical significance was calculated using the Student's t test or ANOVA.

Example 1: Transient Disruption of Retinal Glial Structure by α-AA

Retinal astrocytes and Müller glia are central to the homeostatic and metabolic support of retinal neurons; whereas, after injury these cells develop glial scar that forms critical barriers to neuron regeneration and integration by retinal progenitor cells. A solution of α-AA (1 µg/µl) was injected into the subretinal space of adult wild-type mice. Retinal glial morphology was examined by immunolabeling for glial marker GFAP and assessed the level of GFAP expression by Western blot at day 1-7 post injection. Expression of GFAP is widely detected in the normal mouse retinas (FIG. 1a). A single administration of α-AA effectively eliminated GFAP expression around the injection site at 1-3 days post injection (FIG. 1b), indicating the disruption of the glial barrier structure which may lead to the permissive environment for neuron regeneration and integration by retinal progenitor cells. By day 7, however, GFAP immunostaining reappeared at the injection site and again covered the entire retina (FIG. 1c), suggesting a transient disruption of glial structure followed by repopulation of retinal glial cells after α-AA injection. Western blot quantification of GFAP expression showed significant downregulation in α-AA-injected retinas as compared to normal or saline-injected controls at day 3 post injection, but returned to a control level by day 7 (FIG. 1d).

Figures 1, 10A:
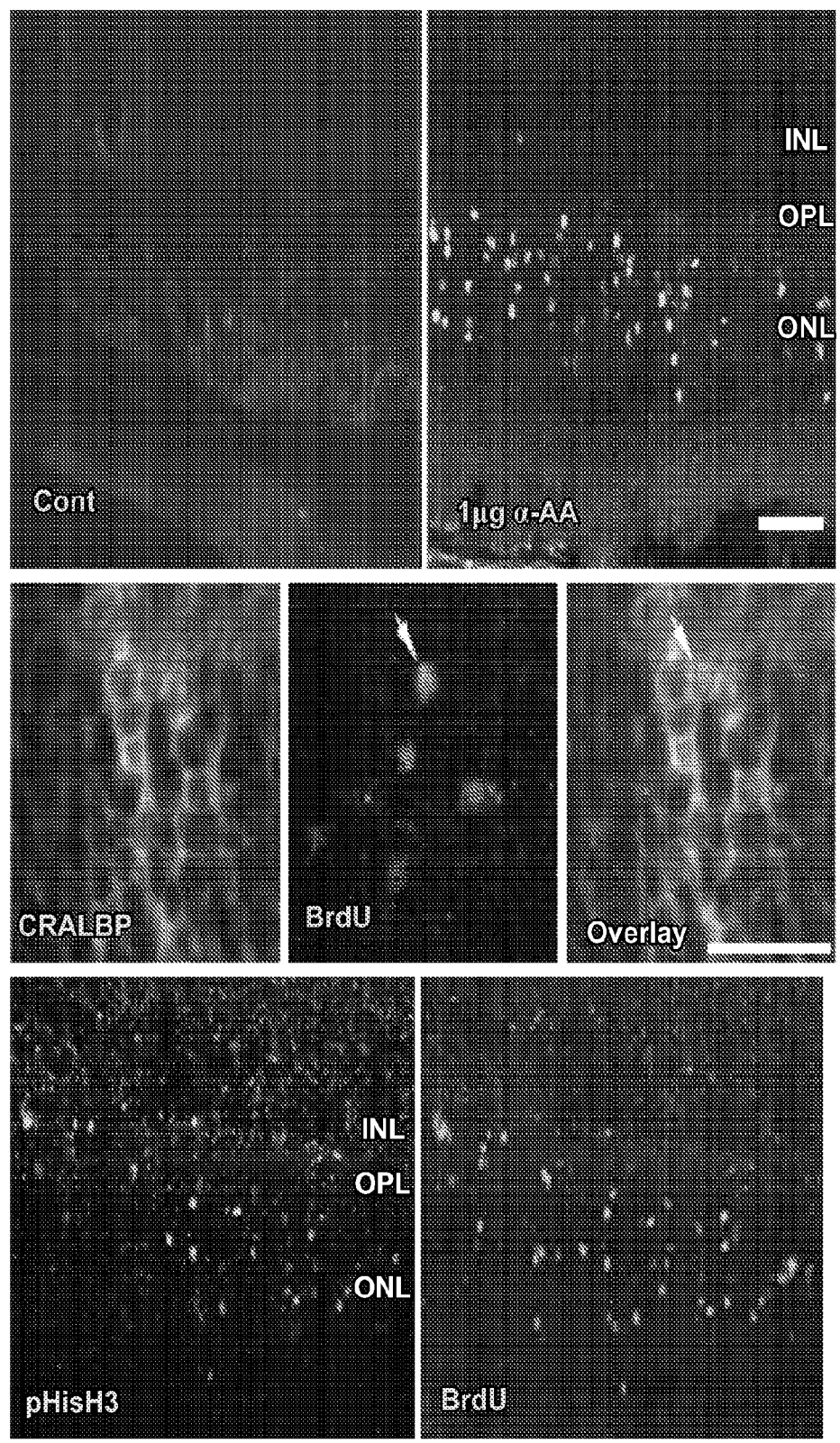
FIGS. 10A and B show fluorescent images and a graph demonstrating that α-AA stimulates Muller cell proliferation.
Figures 2, 10A:
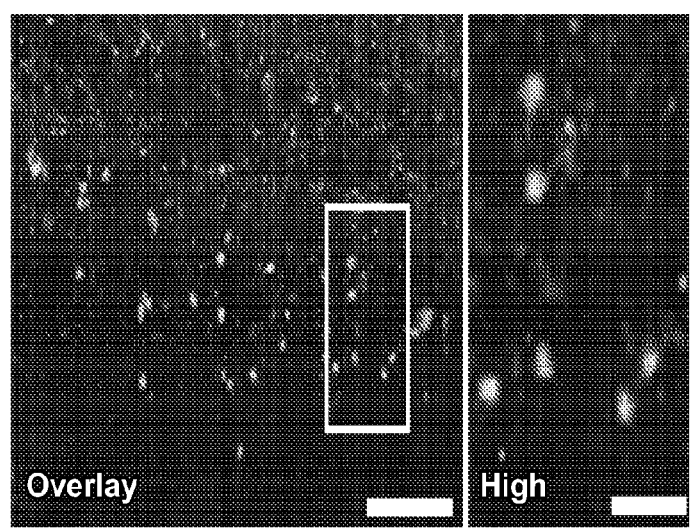

Retinal sections were examined under electron microscopy, in which Müller glia were identified by their characteristic angular nuclei, dense chromatin and dark perinuclear cytoplasm (FIGS. 1e-h). Counts of Müller cell nuclei in their retinal sections revealed 30% reduction in α-AA treated mouse retinas as compared to saline-injected group. No abnormality in retinal neuron morphology was noted. This was also confirmed by immunolabeling for specific markers of retinal neurons, including photoreceptors (recoverin) and amacrine cells (syntaxin) (FIG. 2). No apparent changes in the morphology and lamina structure were observed in α-AA treated retinas as compared to saline-injected controls. These results showed that α-AA induced a temporary elimination of retinal glia without adverse effects on retinal neurons or structure.

Example 2: Robust Grafted Cell Integration into α-AA-Treated Host Retinas

Figure 3A:
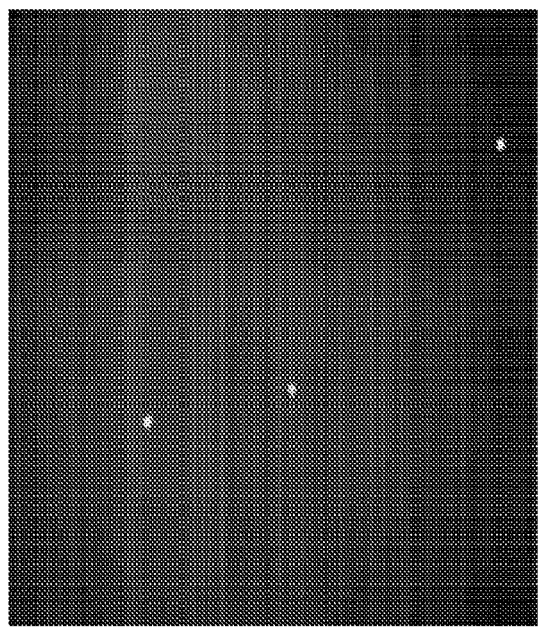
FIGS. 3A-D show fluorescent staining images and graphs demonstrating that robust cell integration following engraftment into the α-AA-treated retinas.
Figure 3B:
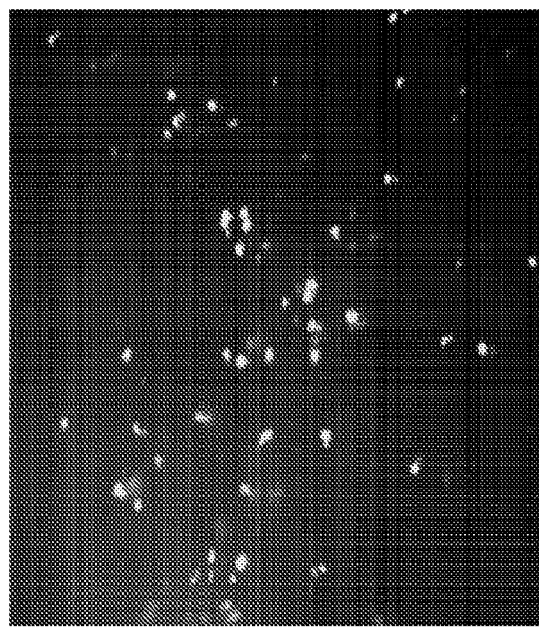
Figure 3C:
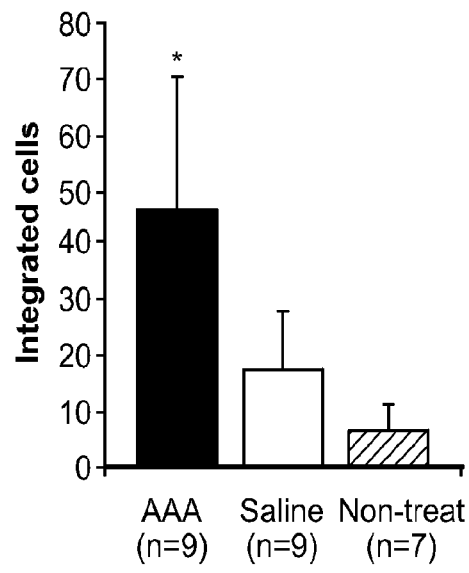
Figure 3D:
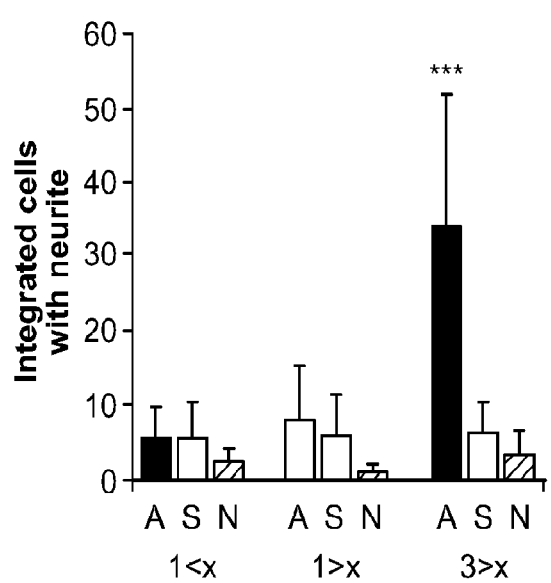

If transient disruption of retinal glia with α-AA promotes morphological integration of grafted retinal progenitors in vivo was next investigated. To distinguish implanted cells from the host environment, retinal progenitor cells were isolated as previously described using P0 mouse pups expressing an enhanced green fluorescent protein (EGFP) transgene driven by a chicken β-actin promoter and cytomegalovirus enhancer. At day 2 following saline or α-AA subretinal injection, retinal cells from P0 EGFP mice were injected into the subretinal space of adult wild-type hosts. Three weeks post transplantation, most donor-derived progenitor cells remained at the injection site and failed to migrate or incorporate into the host retina of the untreated or saline-injected wild-type mice (FIG. 3). In contrast, in α-AA-treated mice, numerous grafted cells had migrated away from the injection site and spread widely into the host retinas. There were 3-5 fold increase in the number of EGFP+ cells repopulated into the α-AA-treated host retina or 7-11 fold increase in number of engrafted cells bearing long neurites (>3 body length), when was compared to either saline-treated or untreated retinas (FIG. 3c). When comparing the efficacy of cell integration following transplantation at various time points post α-AA treatment, it was noted that the number of cells repopulated the host retina was drastically diminished if transplantation was performed after day 5 post α-AA treatment. This was consistent with the timing when GFAP+ cells returned to the host retina after α-AA injection. Thus, in the following studies, cell transplantation was performed at day 2 after α-AA pretreatment when temporal disruption of residential glial structure by α-AA was detected that effectively ameliorates the host barrier to cell integration and promotes grafted cell migration into the host retina.

Figure 6C:
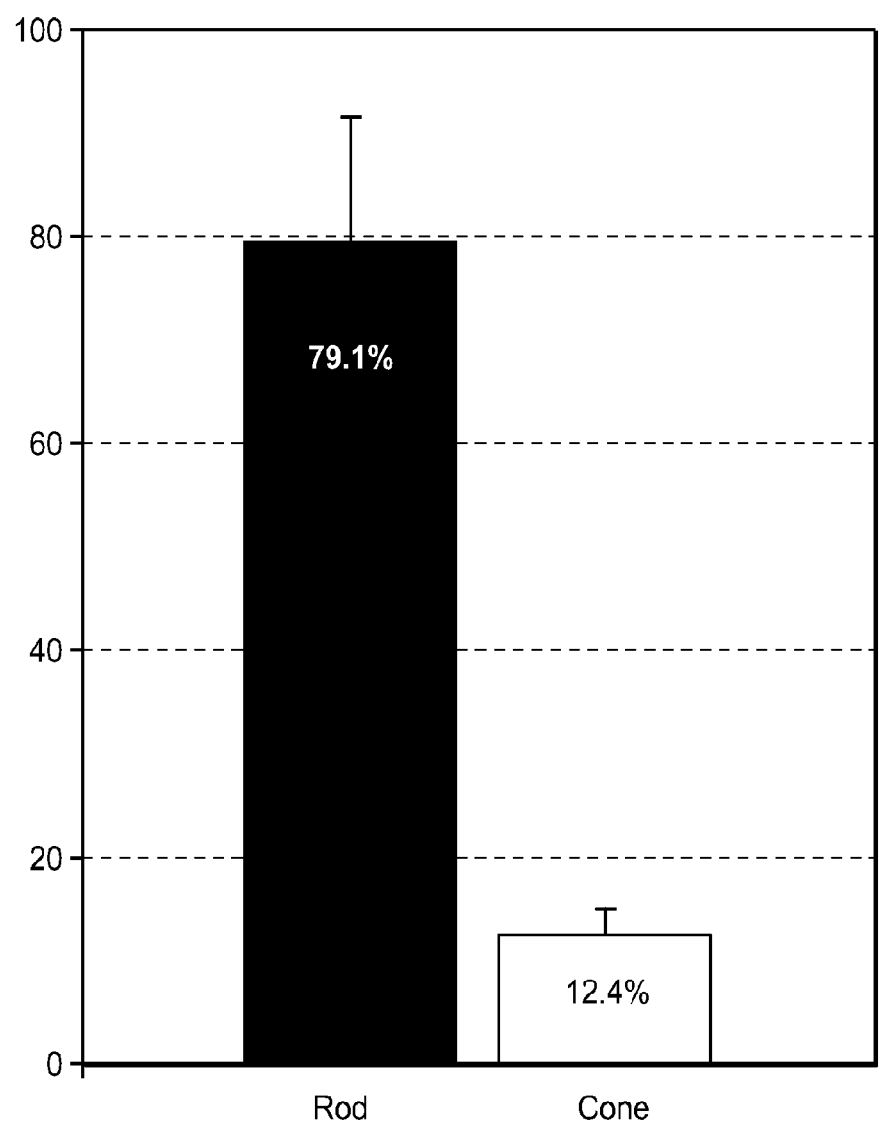

Example 3: Differentiation of Transplanted Retinal Progenitors in α-AA-Treated Host Retinas To determine whether α-AA-treated retina presents a supportive environment that allows appropriate differentiation of retinal progenitors, the behavior of transplanted cells was studied. The fate of transplanted cells was tracked using immunohistochemistry. At day 1 post transplantation, most EGFP+ cells clustered around the injection site and expressed a progenitor cell marker nestin (FIGS. 4a-c). By 21 days post transplantation, grafted cells had integrated into the host, and became positive for mature glial cell marker, GFAP (FIGS. 4d-g), or neuronal markers, Brn-3b (retinal ganglion cells; FIGS. 4h-k) and PCKα (bipolar cells). Many of these cells were localized to the appropriate retinal layers where their corresponding host cells resided. Subretinal injection of α-AA resulted in the majority of grafted cells integrating into the outer nuclear layer (ONL) and expressed the mature photoreceptor cell markers rhodopsin or cone-opsin (FIG. 5). Approximately 80% of the EGFP+ cells that had integrated into the ONL, were positive for rhodopsin, while 12% were cone-opsin positive (FIG. 6). These cells exhibited morphologies characteristics of mature rods or cones, with cell bodies localized within the ONL and inner and outer segments protruding into the inner and outer segment layers. Thus, the host retinal environment in α-AA-pretreated mice is appropriate for integration and differentiation of transplanted retinal progenitors.

Figure 7:
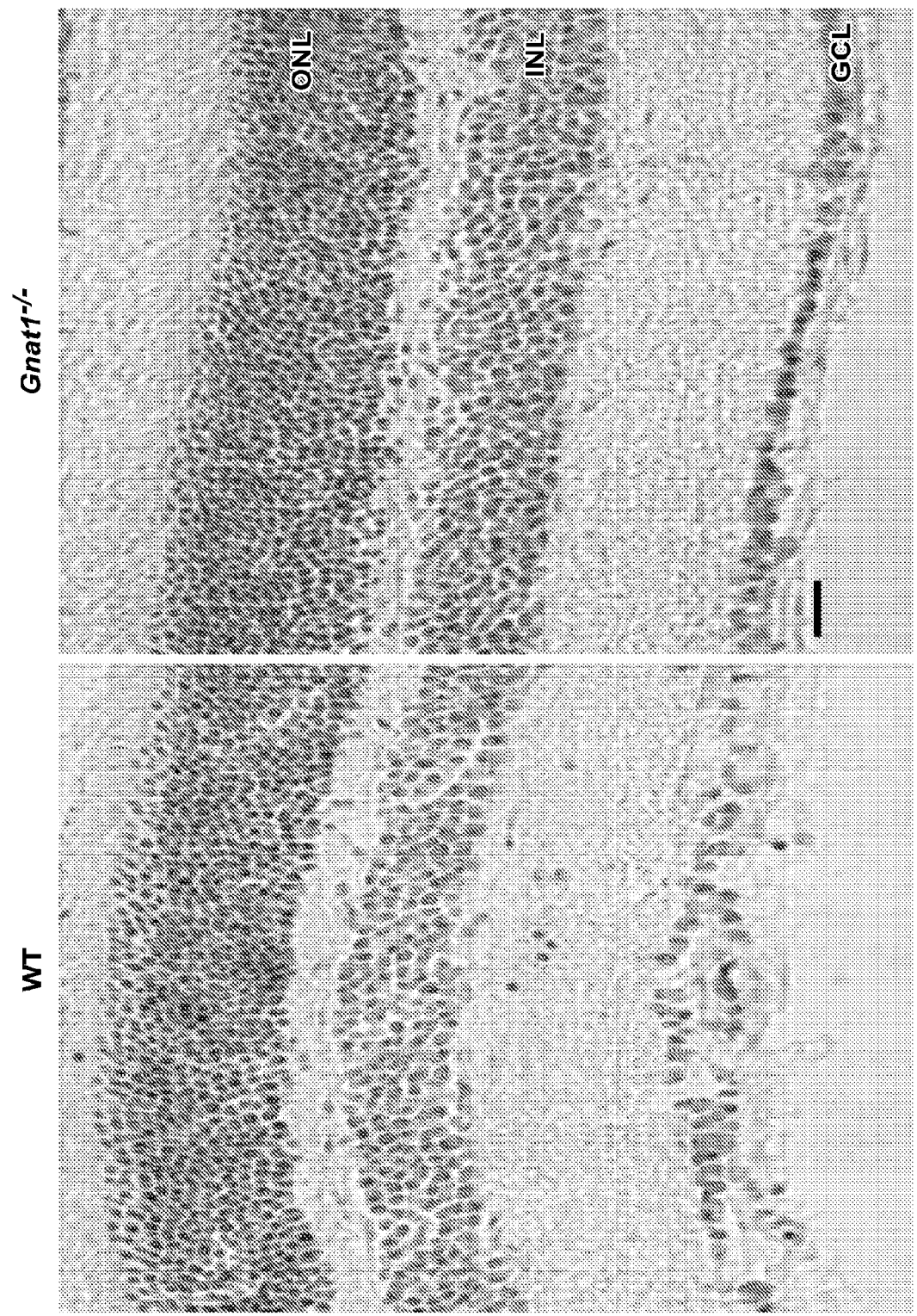
FIG. 7 shows Nissl stained retinal morphology of WT and Gnat1$^{-/-}$ mice. Nissl stained retinal sections of 2-month-old wild-type (WT) and Gnat1$^{-/-}$ mice. The retinas of Gnat1$^{-/-}$ mice revealed normal lamina structure and cell morphology as compared with their WT littermates. Scale bar, 40 μm.

Example 4: Rescue of Photoreceptor Cell Function by Retinal Transplantation in Gnat1$^{-/-}$ Mice A recipient mouse line that carries rod photoreceptor dysfunction, Gnat1$^{-/-}$ mice was used to test whether the integrated cells developed functional connections with the host following transplantation. Gnat1$^{-/-}$ mice display normal retinal lamina structures and morphology (FIG. 7), while they lack an ERG a-wave, a rod photoreceptor cell component in response to light, and exhibits mild photoreceptor degeneration with age. Similar to the results seen in wild-type mice, subretinal injection of α-AA promoted the majority of transplanted cells to integrate into the ONL of adult Gnat1$^{-/-}$ mice. A few grafted cells also incorporated into the inner nuclear layer (INL) of the host retina (FIG. 8$a$) and expressed syntaxin, an amacrine-cell-specific marker, or PKCα, a bipolar cell marker (FIGS. 8$b$-$d$). Almost all cells integrated into the ONL expressed recoverin and rhodopsin, photoreceptor-specific cell markers (FIGS. 8$e$-$l$). By 21 days post transplantation, grafted cells that were integrated into the ONL exhibited a morphology characteristic of mature photoreceptor cells, with their cell bodies residing in the ONL and inner and outer segment-like structures extending into the outer retinal layer. In addition, their inner cellular processes extended to the outer plexiform layer and developed bossom-like morphology (FIG. 9). The terminals of the bossom-like structure could be seen to colocalize with the bipolar cell-specific marker PKCα and synapse marker synaptophysin (FIGS. 9$a$-$d$), demonstrating development of synaptic connections with host bipolar cells.

The ERGs in Gnat1$^{-/-}$ mice before and after retinal transplantation were compared to further determine whether grafted cells established functional connections with the host. Gnat1$^{-/-}$ mice consistently exhibited a flat a-wave and absence of rod photoreceptor response with light stimulation (FIG. 9$h$). By 21 days post transplantation, a typical a-wave was detected in Gnat1$^{-/-}$ mice that received retinal progenitor cell transplantation and α-AA pretreatment; however, Gnat1$^{-/-}$ mice that had received saline-pretreatment and retinal progenitor cell transplantation exhibited a flat a-wave (FIG. 9$h$) or absence of light-induced rod ERG component. Thus, retinal transplantation into α-AA-pretreated retina restored rod photoreceptor cell function, while those into a control or saline treated retina failed to do so, which is consistent with the lack of morphological integration in the latter case. Together, these results indicate that α-AA promoted not only morphological, but also functional integration of grafted retinal progenitors that enabled restoration of light-induced photoreceptor cell responses in Gnat1$^{-/-}$ mice.

Example 5: Subretinal Injection of Alpha-Aminoadipate Rescues Light-Evoked Retinal Activities in Mice with Photoreceptor Dystrophy Mice carrying rhodopsin deficiency (Rho$^{-/-}$) were used to determine if injection of alpha-aminoadipate (αAA) is sufficient to induce neuroregeneration from endogenous retinal progenitors, e.g., Muller cells, leading to preservation and restoration of photoreceptor cell function. Light-evoked photoreceptor responses and retinal functions in Rho$^{-/-}$ mice that received αAA or saline injection were assessed using ERGS and whole cell-attached patch clamp.

Rho$^{-/-}$ mice exhibited vision loss characteristic of retinitis pigmentosa in human patients, the most common type of retinal degeneration in young adults. The phenotype is characterized by an initial loss of night vision as a result of the malfunction and death of rods, followed by a progressive loss of cones. Postnatal Rho$^{-/-}$ mice displayed slow degeneration of retinal photoreceptor cells over a 3 month period that first manifests in rod photoreceptors due to specific genetic defect in rods; the death of rods leads to eventual cone degeneration. Functionally, these mice showed the absence of rod-induced ERG component or flat a-wave that is accompanied by graduate decline of b-wave when the retina loses their cone photoreceptors. At 10-12 weeks old, their ERGS become extinct due to complete loss of both rods and cones.

Similar to that occurring in human patients with retinitis pigmentosa, the mutation in Rho$^{-/-}$ mice was restricted to rods. Thus, new cones generated by endogenous retinal progenitors under these conditions are genetically normal and can contribute directly to vision restoration. Moreover, new rods generated by endogenous retinal progenitors, albeit carry a gene deficiency associated with rods, serve the purpose for supporting cone survival, thus preserving vision, as a result of increased number of rods. Because cones are responsible for color and high-acuity vision, it is their preservation and restoration that is critical for improvement of vision and thus the quality of life.

To determine if αAA induces functional neuroregeneration in Rho$^{-/-}$ mice, αAA was injected subretinally into the left eyes of 6 week-old Rho$^{-/-}$ mice, while their contralateral eyes were injected with saline and served as controls. After a 4 week survival period to allow regeneration of new photoreceptors, mouse ERG was measured in both eyes and then performed immunohistochemistry to identify photoreceptor cells. Rho$^{-/-}$ mice lack the rod photoreceptor cell component or ERG a-wave. As cones consist of ~3% of photoreceptors in mice, it is difficult to assess cone action a-wave; therefore, flicker ERG photometry under cone-isolation conditions was used to measure cone functions. The eyes treated with αAA exhibited sizable b-wave during ERG measurement, while in contrast, the contralateral (control) eye that received injection of saline revealed much diminished or almost distinct ERG b-wave (FIGS. 14A-D). The ERG b-wave arises from neural activity downstream of photoreceptors, its presence in the αAA treated eye has a very important implication: not only is the treatment creating new or preserving existing photoreceptors, such photoreceptors are integrating into the existing retinal circuitry in such a way as to elicit activity in downstream neurons (most likely bipolar cells).

Figure 15D:
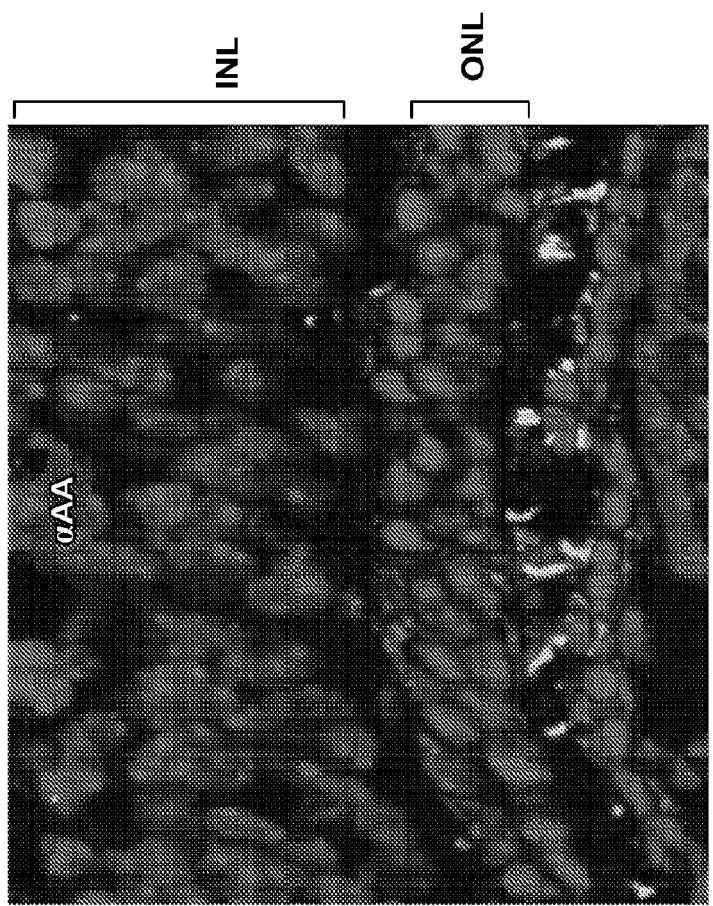
Figure 15C:
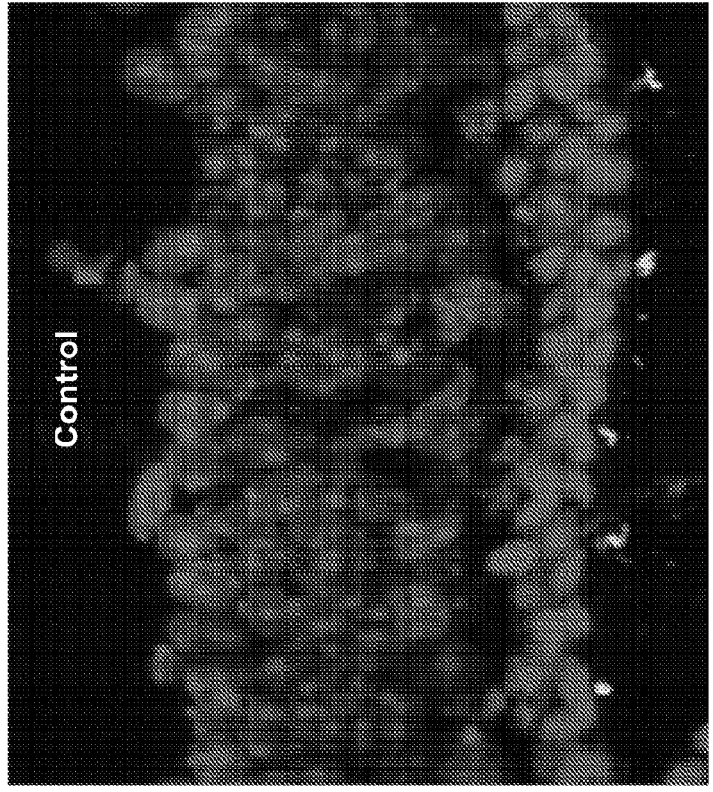

To further explore the function of downstream neuron activities and demonstrate the photoreceptor integration or preservation of retinal circuitry by αAA, the retinas were extracted from both saline- and αAA-treated eyes for a series of in vitro measurements (via cell-attached patch clamp). Consistent with the presence of ERG b-waves in αAA-treated eye, light-elicited spiking responses in some of the ganglion cells were observed (n=4/9) (FIGS. 15A, B). Similar to findings from other types of retinal degenerative mice, an elevated level of background firing in these cells, likely due to the changes in the excitability of the presynaptic network formed by bipolar cells and amacrine cells, were also observed. In contrast, no light-elicited responses in ganglion cells were recorded from the saline-injected eyes (n=4/4, FIG. 14C). Likewise, small strong b-waves together with measured light responses in the αAA-treated eye was further supported by the observation of an increased number of cone photoreceptor cells as compared to saline-treated control mice (FIGS. 15C, D). These data show that αAA treatment leads to the preservation or restoration of cone photoreceptors and light-induced responses in the diseased retinas. Additional vision and optomotor tests known in the art are conducted to assess vision restoration, such as the water maze test. Thus, a single intraocular injection of αAA may be sufficient to improve vision, in part by increasing the number of cones. Moreover, αAA does not cause apparent retinal neuron damage.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preserving, restoring, or enhancing vision of a subject, comprising administering to an injured or diseased eye of said subject a composition comprising alpha-aminoadipate, wherein said composition is administered at a dosage less than 500 μM, wherein said preserving, restoring, or enhancing vision is measured by electroretinography (ERG), patch-clamp recording, Snellen chart or E chart.

2. The method of claim 1, wherein said preserving, restoring, or enhancing vision of a subject comprises increasing photoreceptor activity, increasing photoreceptor regeneration, increasing the number of retinal progenitor cells, increasing the number of retinal neurons, replacing lost or damaged retinal neurons or retinal cells, increasing light retinal response, increasing light perception/detection, or increasing visual acuity.

3. The method of claim 1, wherein the subject is suffering from an ocular injury or ocular disease associated with vision loss, retinal cell damage, or retinal degeneration.

4. The method of claim 3, where the retinal degeneration comprises photoreceptor degeneration.

5. The method of claim 3, wherein said ocular injury or disease comprises macular degeneration, diabetic retinopathy, retinitis pigmentosa, cone dystrophy geographic atrophy, detachment ischemia, optic nerve neuritis, ocular cancer, glaucoma, retinal trauma, physical trauma to the optic nerve and surrounding tissues, or retinal nerve damage.

6. The method of claim 1, wherein the administration comprises subretinal injection, intravitreal injection, subconjunctiva injection, or intraocular injection.

7. The method of claim 1, wherein the composition increases proliferation, migration, de-differentiation, or differentiation of Muller cells, ciliary epithelial cells, retinal pigment epithelial cells, bone marrow-derived stem cells, or mesenchymal stem cells.

8. The method of claim 1, wherein the composition is administered at a dosage of 0.1-350 μM.

9. The method of claim 1, wherein the composition is administered at least once.

10. The method of claim 1, wherein the composition is administered once every 3-5 days.

11. The method of claim 1, further comprising transplanting retinal cells after administering said composition.

12. The method of claim 1, wherein the composition is administered at a dosage less than 350 μM.

13. A method for preserving, restoring, or enhancing vision of a subject, comprising administering to an injured or diseased eye of said subject a composition comprising alpha-aminoadipate, wherein said composition is administered at a dosage less than 500 μM, wherein said preserving, restoring, or enhancing vision of a subject comprises an increase in photoreceptor activity and wherein said photoreceptor activity is measured by ERG.

14. The method of claim 13, wherein said preserving, restoring, or enhancing vision of a subject comprises an increase in b-waves as measured by ERG analysis.

* * * * *